(12) United States Patent
Reichmuth

(10) Patent No.: US 9,011,799 B2
(45) Date of Patent: Apr. 21, 2015

(54) LABORATORY SAMPLE INSTRUMENT WITH PRINTED CIRCUIT BOARD CABLE DEVICE

(75) Inventor: Burkhardt Reichmuth, Hamburg (DE)

(73) Assignee: Eppendorf AG, Hamburg (DE)

( * ) Notice: Subject to any disclaimer, the term of this patent is extended or adjusted under 35 U.S.C. 154(b) by 44 days.

(21) Appl. No.: 13/572,001

(22) Filed: Aug. 10, 2012

(65) Prior Publication Data
US 2013/0052099 A1 Feb. 28, 2013

Related U.S. Application Data

(60) Provisional application No. 61/522,292, filed on Aug. 11, 2011.

(30) Foreign Application Priority Data

Aug. 11, 2011 (DE) .......................... 10 2011 109 992

(51) Int. Cl.
| | |
|---|---|
| *G01F 19/00* | (2006.01) |
| *G01L 3/02* | (2006.01) |
| *H05K 1/02* | (2006.01) |
| *G01F 11/02* | (2006.01) |
| *B01L 3/02* | (2006.01) |

(Continued)

(52) U.S. Cl.
CPC .......... *H05K 1/0296* (2013.01); *G01N 35/1002* (2013.01); *G01F 11/021* (2013.01); *H05K 1/0393* (2013.01); *H05K 2201/09027* (2013.01); *H05K 2201/09236* (2013.01); *H05K 2201/0939* (2013.01); *H05K 2201/09672* (2013.01); *H05K 2201/10151* (2013.01); *B01L 3/0227* (2013.01); *B01L 2200/087* (2013.01); *B01L 2200/12* (2013.01)

(58) Field of Classification Search
CPC ........................... G01N 35/10; G01N 35/1002
USPC ..................... 422/509, 518; 73/1.74
See application file for complete search history.

(56) References Cited

U.S. PATENT DOCUMENTS 4,567,780 A * 2/1986 Oppenlander et al. ..... 73/864.16
5,620,661 A 4/1997 Schürbrock
(Continued)

FOREIGN PATENT DOCUMENTS

DE 10 2004 023 866 B3 2/2006
DE 20 2006 019 817 U1 4/2007
(Continued)

*Primary Examiner* — Jill Warden
*Assistant Examiner* — Brittany Fisher
(74) *Attorney, Agent, or Firm* — Arnold & Porter LLP; Todd A. Lorenz

(57) ABSTRACT

The invention relates to a laboratory sample instrument with a cable holding space in which a printed circuit board cable device is arranged. The printed circuit board cable device has at least one printed circuit board with first and second sides and, arranged in succession, at least one first circuit board section, at least one second circuit board section and at least one third circuit board section, and with a number of conductor tracks arranged in parallel with respect to one another and extending from a first track section arranged in the first circuit board section, via the second circuit board section to the third circuit board section, in which a second track section is arranged, wherein, in the second circuit board section, at least one conductor track is arranged on the first side of the board and at least one track is arranged on the second side.

10 Claims, 10 Drawing Sheets

(51) Int. Cl.
  *G01N 35/10* (2006.01)
  *H05K 1/03* (2006.01)

(56) References Cited

U.S. PATENT DOCUMENTS

| | | | |
|---|---|---|---|
| 5,892,161 A * | 4/1999 | Conley et al. | 73/864.18 |
| 6,019,004 A * | 2/2000 | Conley et al. | 73/864.16 |
| 6,396,709 B1 | 5/2002 | Schmich | |
| 7,773,122 B2 | 8/2010 | Irion et al. | |
| 8,114,361 B2 | 2/2012 | Reichmuth | |
| 8,187,171 B2 | 5/2012 | Irion et al. | |
| 2005/0118069 A1 * | 6/2005 | Solotareff et al. | 422/100 |
| 2008/0034898 A1 * | 2/2008 | Molitor et al. | 73/864.16 |
| 2008/0156117 A1 * | 7/2008 | Londo et al. | 73/864.14 |

FOREIGN PATENT DOCUMENTS

| | | |
|---|---|---|
| GB | 2 157 085 A | 10/1985 |
| WO | WO 98/14979 A1 | 4/1998 |
| WO | WO 99/65548 A1 | 12/1999 |

* cited by examiner

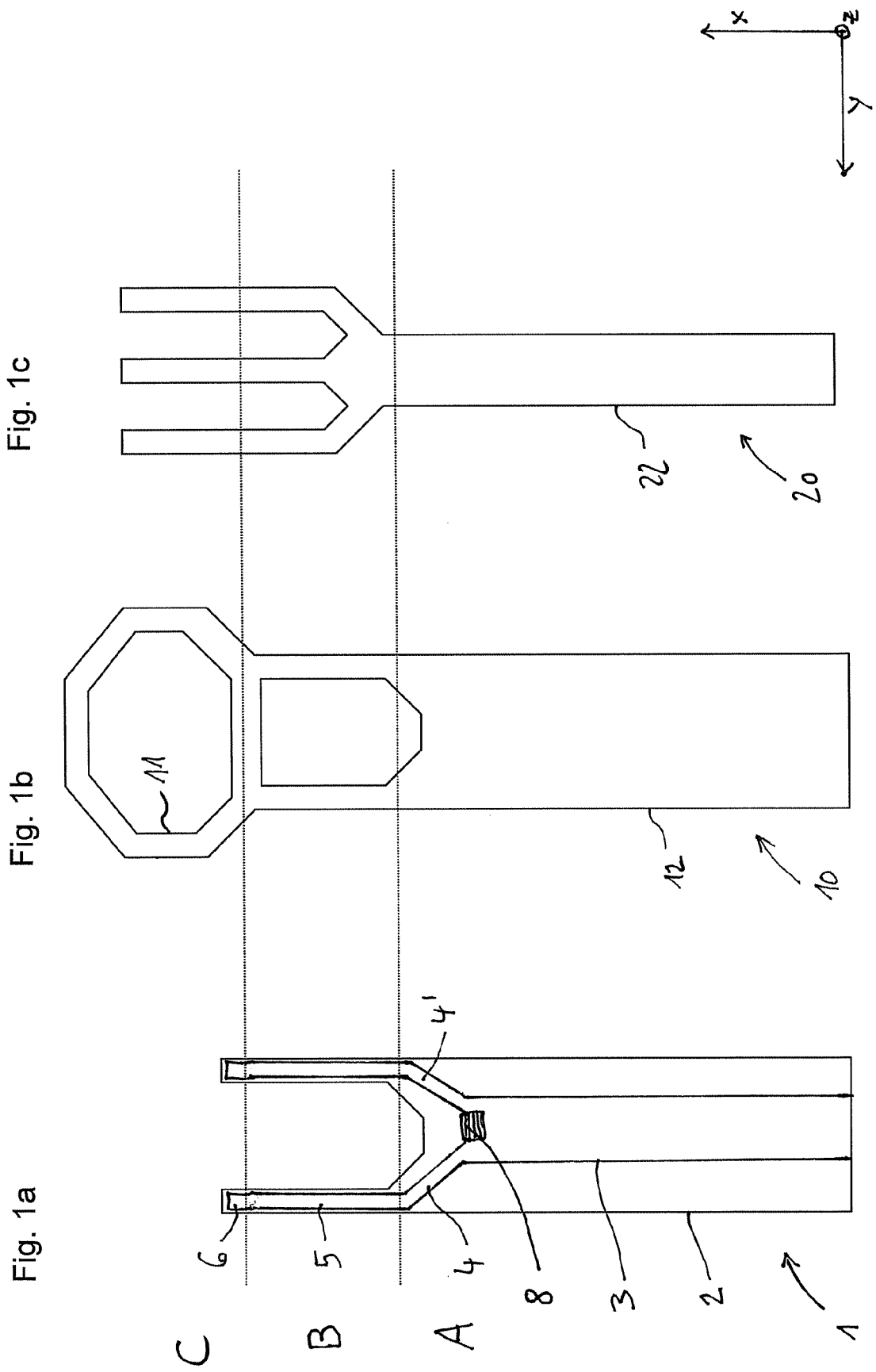

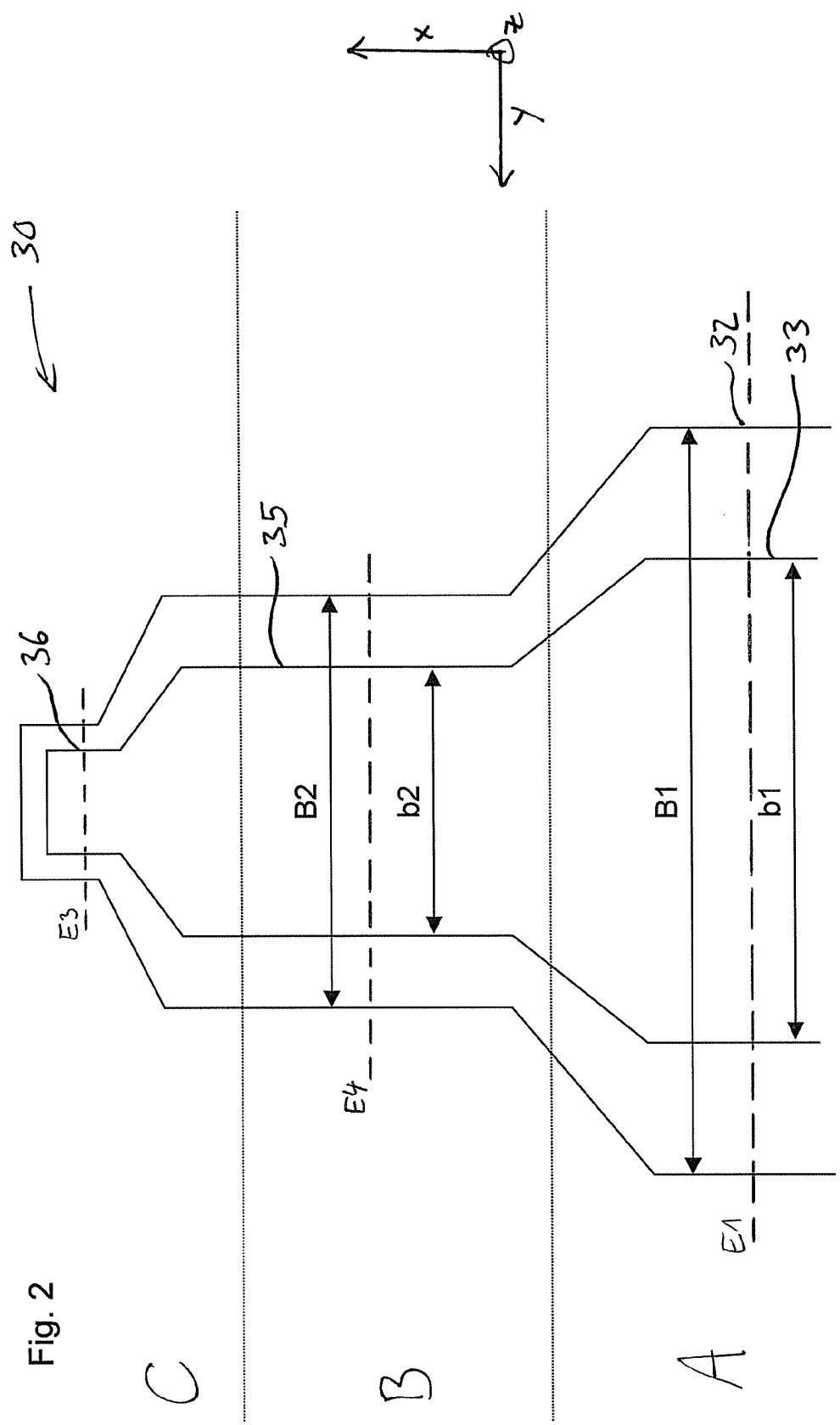

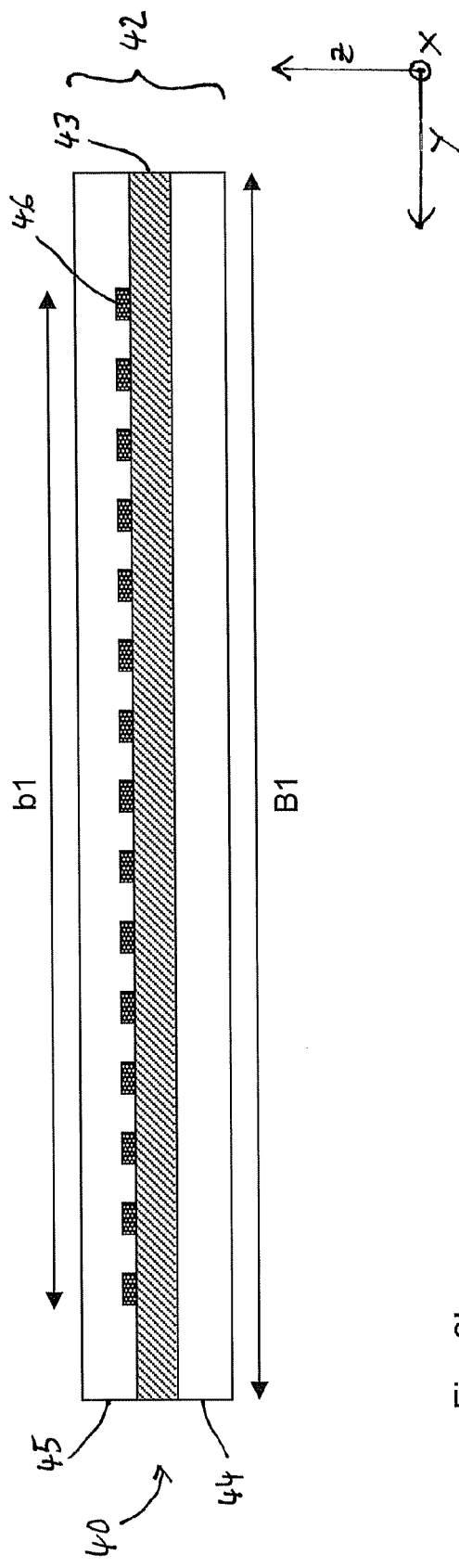
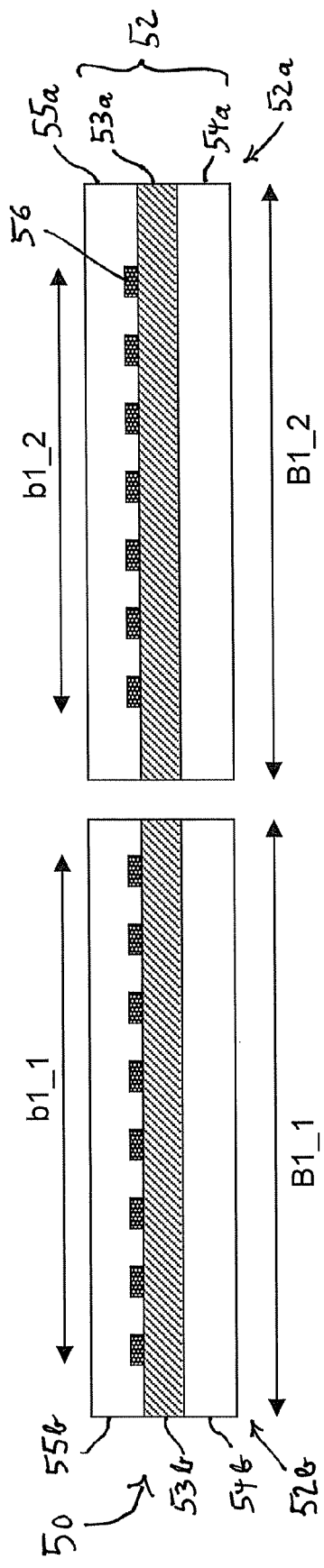
Fig. 3a
Fig. 3b

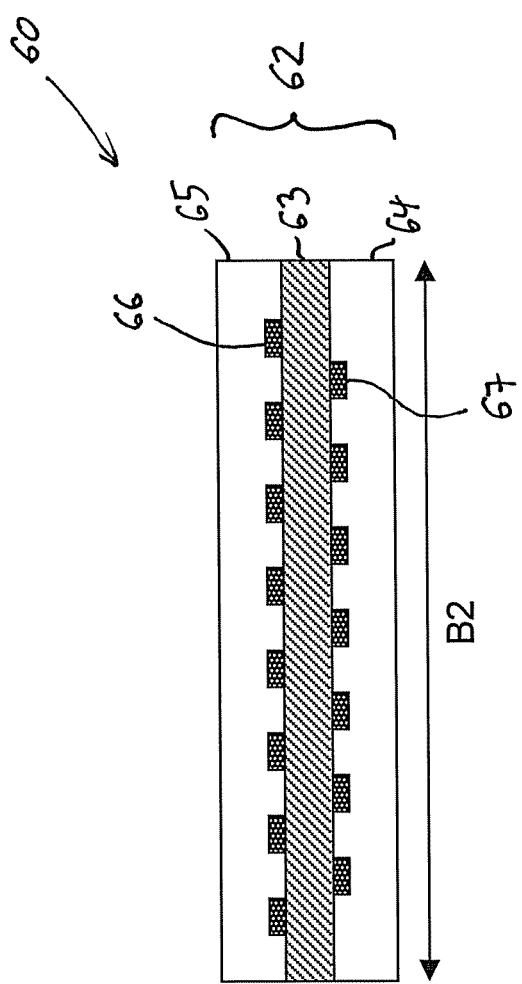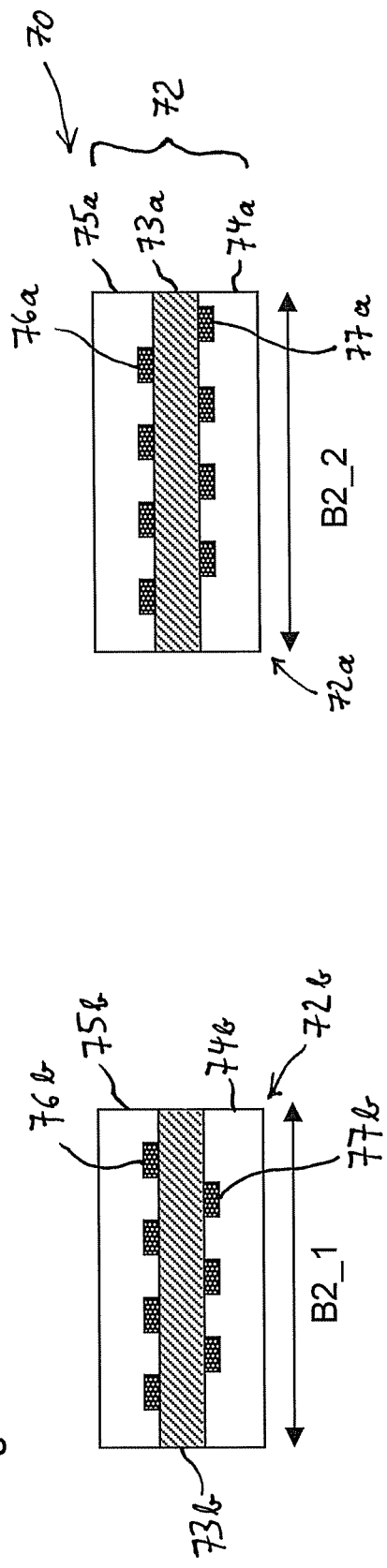

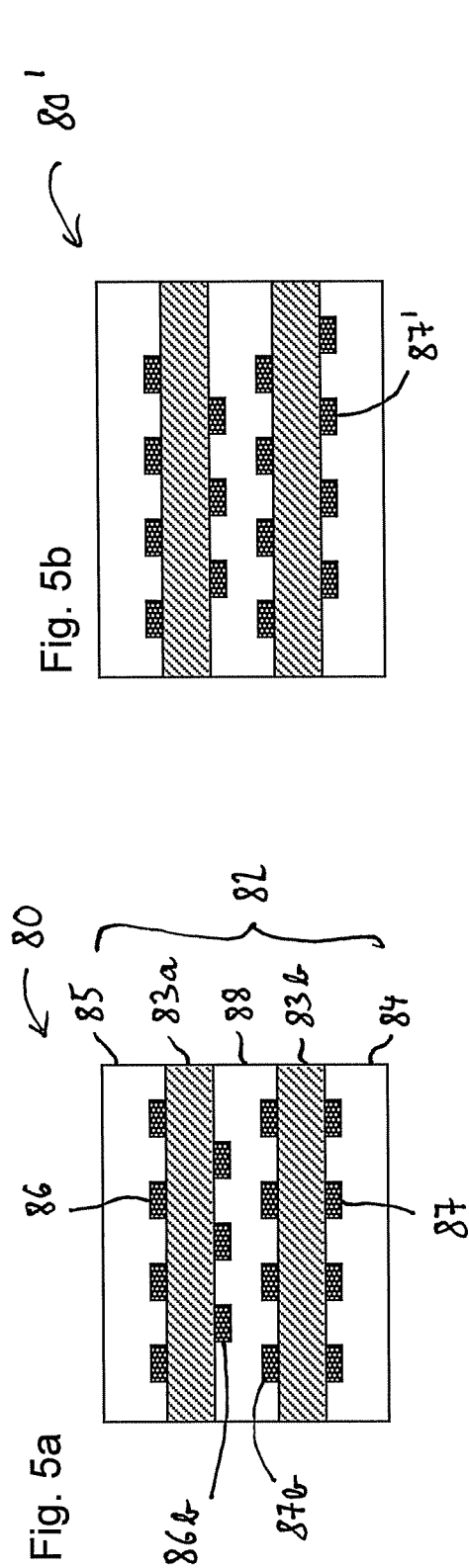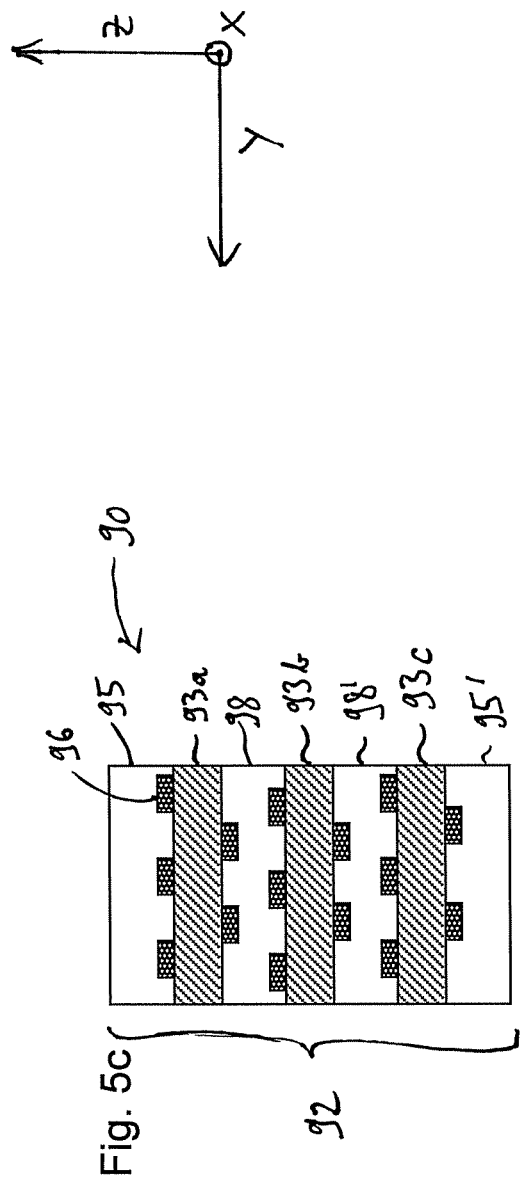

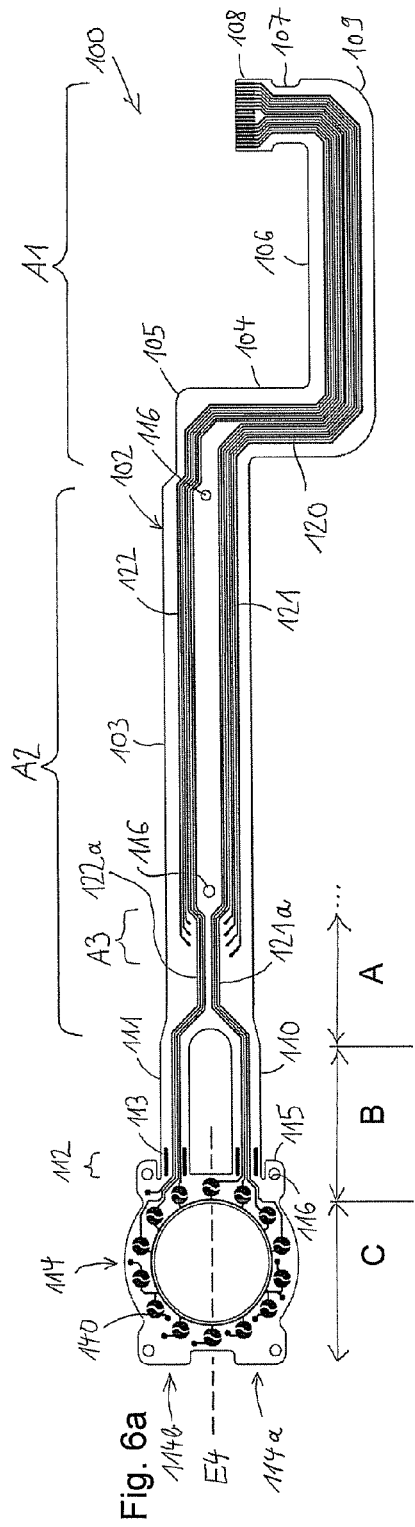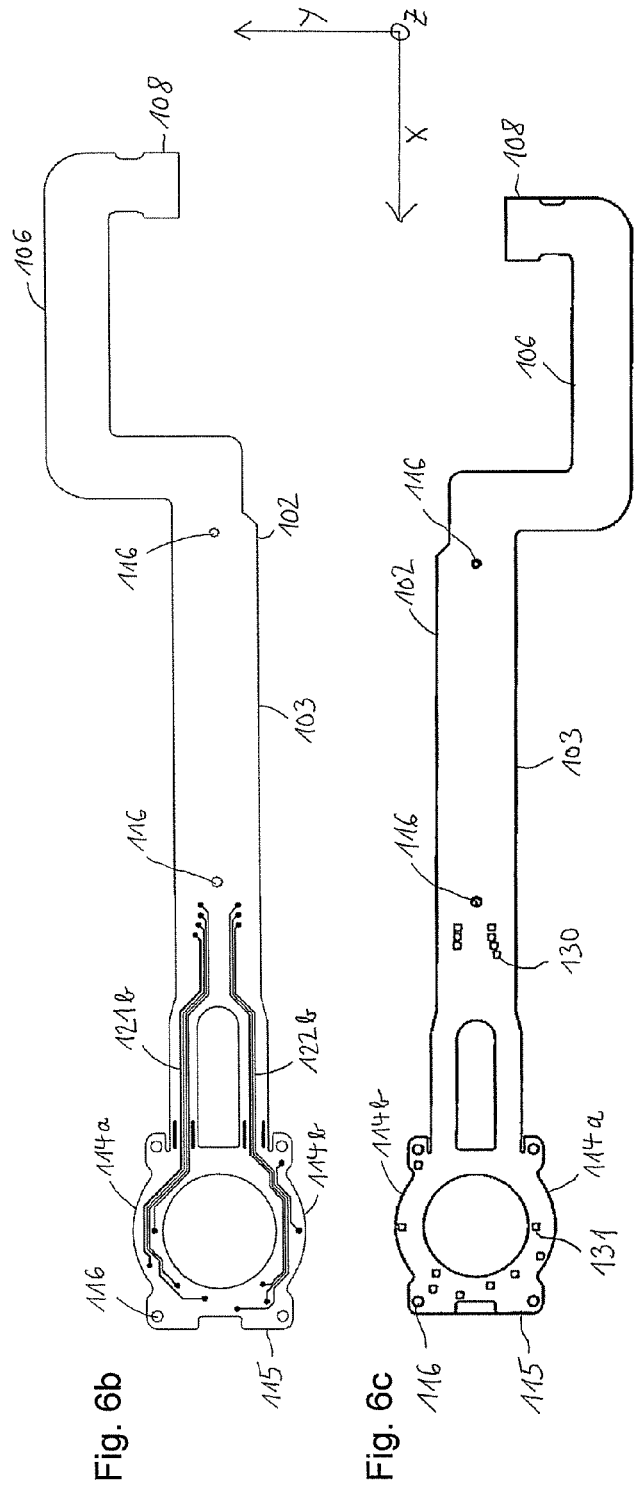
Fig. 6a  Fig. 6b  Fig. 6c

Fig. 7a
Fig. 7b
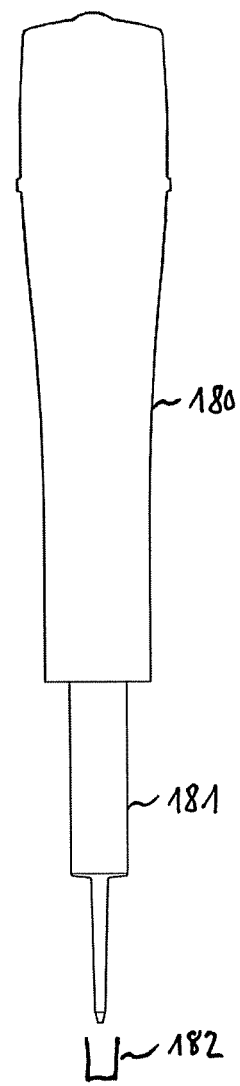
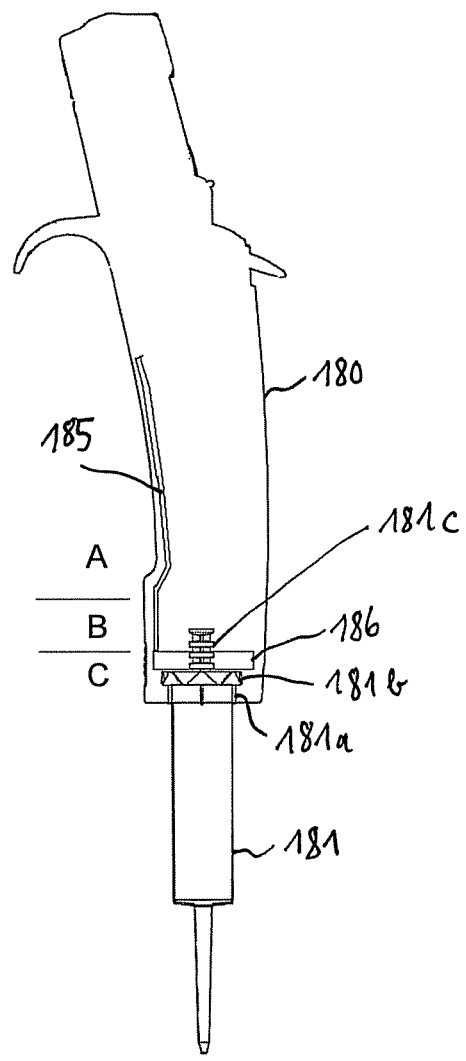
PRIOR ART

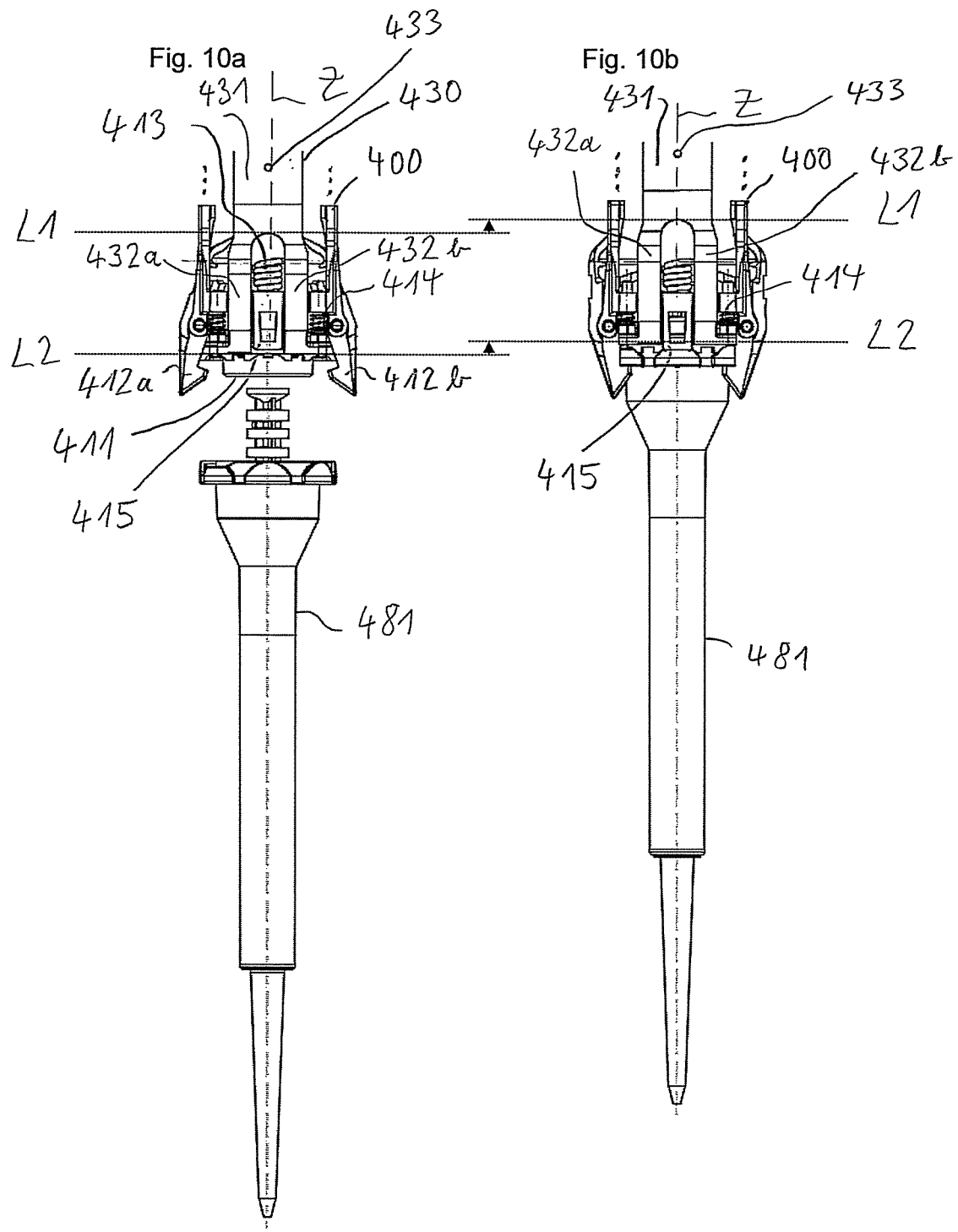

LABORATORY SAMPLE INSTRUMENT WITH PRINTED CIRCUIT BOARD CABLE DEVICE

The present invention relates to a laboratory sample instrument with a printed circuit board cable device, more particularly to a metering device, e.g. a dispenser or a pipette, with a printed circuit board cable device.

Such laboratory sample instruments can be instruments for apparatus-based processing or examination of laboratory samples. Flexible printed circuit board cable devices afford the advantage of enabling cabled signal connections and other technical lines even if, e.g. for reasons of space, only a very small or flat cable cross section is possible. The spatial volume claimed by a laboratory sample instrument is usually very large compared to that of the laboratory sample itself. Therefore, the laboratory sample instrument tapers in the direction towards the laboratory sample in most cases. By way of example, this is the case in manual metering devices, which a user can hold in one hand, in which a moveable drive mechanism and an adjustment mechanism, the latter controlling the movability of the drive mechanism, are housed in the shaft of the instrument which also serves as a handle. As a result of the risk of contamination by the laboratory sample instruments, the means in which the laboratory sample is held is preferably a replaceable part, usually a disposable part, for example made of plastic. The latter should be connected to the laboratory sample instrument by a holding device. The holding device is situated at one end of the laboratory sample instrument, at which end the laboratory sample is held and emitted. The means in which the laboratory sample is held is preferably a pipette tip or a syringe with syringe body and syringe piston. However, other means, e.g. cartridges, are also possible.

Pipette tips are usually placed onto an attachment which usually has an at least slightly conical design but can, inter alia, also have a cylindrical design. The pipette tip is placed onto the attachment such that the tip lies tightly against the attachment and preferably no air can pass between attachment and pipette tip. The attachment is the outermost part on the housing part of the laboratory sample instrument, in which a piston-cylinder unit is provided as displacement device, with the cylinder unit preferably being formed by the housing part of the laboratory sample instrument. In the cylinder, a column of air is moved by the piston, as a result of which the laboratory sample is taken up into and/or emitted from the pipette tip. If an electric apparatus, for example a sensor apparatus for identifying the utilized pipette tip, should be attached to the attachment for holding the pipette tip, there is only very little space directly on the housing part for laying electric lines to the sensor apparatus so that the latter can communicate with a closed/open-loop control apparatus within the housing of the laboratory sample instrument. The space available for conventional electric feed lines or the opening cross section in the vicinity of the electric apparatus can therefore be too small or the arrangement geometry only allows a small line cross section there.

DE 43 42 178 C2 describes such a laboratory sample instrument, namely a repeater pipette, which is also referred to as a manual dispenser and operates according to the principle of direct displacement. Unlike in a pipette, which works on the air-cushion principle, the displacement piston in a manual dispenser is not arranged in the instrument shaft, but rather it is part of the means in which the laboratory sample is held, which means is embodied in the style of a syringe. Such a dispenser operates according to the direct displacement principle. Here, the displacement piston of the syringe is essentially not separated from a sample liquid by an air cushion when metering the sample liquid, but rather it is in direct contact therewith, as a result of which particularly accurate metering is possible. The displacement piston belonging to the means is coupled to an actuator which is arranged in the instrument shaft. In particular, the additional advantage of the syringe as per the aforementioned document lies in the fact that the attachment section on the cylindrical syringe body of the syringe for attaching the latter to the manual dispenser is additionally embodied as an information carrier. A sensor arranged in the head section of the manual dispenser reads out the information and provides it to the control apparatus, which is arranged in the instrument shaft. The information carrier and the sensor are used to capture automatically the type of syringe that the user is connecting to the manual dispenser. This information is used by the control apparatus to select the control program which converts the desired sample volumes, predetermined by the user, into corresponding piston movements.

The sensor uses a scanning apparatus, which reads out a number of readout regions on the syringe. The readout regions are arranged concentrically around the piston axis on the connection side of the syringe and face the head section of the manual dispenser. Each readout region has (or does not have) a projection, which activates (or does not activate) a mechanical contact switch of the sensor and thus closes (or does not close) an electric circuit. The sensor has seven contact points, which each correspond to one readout region and by means of which the desired information is encoded. These contact points are arranged concentrically on a sensor printed circuit board, which has an annular design and to the annular face of which the piston axis runs perpendicularly. A conductor track film is attached to the edge of the sensor printed circuit board at right angles to the annular face thereof and routes the electric lines from the contact points to a control apparatus situated higher up in the instrument shaft. Often only relatively little space is available in the transition region between sensor printed circuit board and conductor track film for the purpose of coupling, e.g. by soldering, the electric lines of the sensor printed circuit board to those of the conductor track film. This spatial problem becomes even more pronounced with increasing number of sensor points and increasing number of required lines.

It is the object of the present invention to provide a laboratory sample instrument, which can be configured with more flexibility regarding the space available inside the instrument, which, in a particular aspect, affords the possibility of connecting electric conductors to an electric apparatus arranged at a distance from these electric conductors inside the laboratory sample instrument, even over a spatial segment with a restricted amount of space available.

According to the invention, this object is achieved by the laboratory sample instrument as per claim 1. Preferred embodiments are the subject matter of the dependent claims.

In particular, laboratory sample instruments according to the invention, more particularly manual laboratory sample instruments, can be configured more flexible, offering either more functionality and/or a more compact design, or, respectively, providing a better ratio of functionality and size. This is because the cable holding space of the laboratory sample instrument can be configured compact, in particular the second holding space can be configured compact. This is achieved by providing a printed circuit board cable device, which has a rather compact and functional design, in particular regarding the second printed circuit board section. The surface available on a second printed circuit board section is utilized in an optimal manner. In particular, the size and shape of the second printed circuit board section is adapted to the second holding space. This way, a laboratory sample instrument according to the invention can be constructed more flexible, wherein the second printed circuit board section, for reasons of space or for other reasons, e.g. as a result of other construction requirements, can be restricted to a second width dimension which is less than a first width dimension of the first printed circuit board section.

The first track section of the conductor tracks can be the one end of the conductor tracks, which e.g. can lead to a plug apparatus which can serve for contacting socket apparatuses. By way of example, these socket apparatuses can be assigned to a control apparatus of the laboratory sample instrument. The second track section of the conductor tracks can be the other end of the conductor tracks at which, for example, electric contact apparatuses or sensor elements of a sensor apparatus can be arranged.

Laboratory sample instruments in particular can have a space for holding cables which, at least in a second spatial region, is smaller than in a first spatial region. As described at the outset, such laboratory sample instruments are preferably metering devices, for example pipettes or dispensers, more particularly manually operable pipettes or dispensers. Such manually operable instruments are referred to as manual laboratory sample instruments. Examples of manual dispensers include the laboratory sample instruments "Multipette® stream" and "Multipette® Xstream", which are electrical dispensers, commercially distributed in Germany in 2011 by Eppendorf AG. The invention is also suitable to be adapted to a laboratory sample instrument of the type described in the document DE 43 178 C2, mentioned at the outset. However, the invention can also relate to those laboratory sample instruments in which a liquid, gel-like or powdery laboratory sample is worked on, processed, held and/or emitted and/or transported and/or even only examined, for example examined by optical and/or electric or electromagnetic means.

The printed circuit board is preferably deformable, preferably flexible, and more particularly elastic. The printed circuit board preferably has a flexibility which is suitable for bending the printed circuit board in a non-destructive fashion with a bend radius, with the direction of this radius preferably running perpendicularly to the conductor tracks. As a result of the flexibility of the printed circuit board, the printed circuit board cable device can, as a result of bending, more easily be arranged in cramped spatial conditions, which typically exist in a laboratory sample instrument of the aforementioned type. By way of example, the bend radius can lie between 0.5 mm and 100 mm and preferably lies between 1.0 mm and 30.0 mm.

A flexible printed circuit board has a flexible substrate, which is preferably made of a polyimide, e.g. of DuPont™ Kapton®. However, it is also possible to provide other materials, e.g. polyesters e.g. PET or PEN. The thickness (height) of the printed circuit board is preferably between 20 µm and 75 µm, preferably between 25 µm and 60 µm, and more particularly 50 µm (±5 micrometers). "Flexible Printed Circuits" ("FPCs") are also possible flexible printed circuit boards.

The printed circuit board sections are arranged in succession, i.e. the first printed circuit board section is connected to the second one and the second one is connected to the third one. All or at least two printed circuit board sections preferably have an integral design or have at least a common flexible substrate.

The conductor tracks on the printed circuit board are preferably, at least in sections, applied parallel with respect to one another on the surface of the flexible substrate. To this end, the conductive material of the conductor tracks, for example a metal, e.g. copper or gold, or a metal alloy preferably made of gold and nickel, is connected to the surface, for example by vapour deposition. The height (=thickness) of the conductor tracks with respect to the printed circuit board is, at least in sections or at least during the first production step, substantially constant and is preferably between 20 µm and 75 µm, preferably between 25 µm and 55 µm and preferably between 30 and 40 µm. The width of the conductor tracks is substantially constant, at least in sections, and is more particularly between 50 µm and 350 µm, preferably between 300 µm and 100 µm or preferably between 250 µm and 150 µm. The printed circuit board or a printed circuit board section preferably has, at least in sections or overall, a planar design. In particular, a preferably provided bend in the printed circuit board is only made after the production of the printed circuit board cable device. A printed circuit board section, more particularly the second one, can have at least one bent place, at which the printed circuit board section is bent with a bend radius. The width of the conductor tracks in a bent printed circuit board section is preferably wider—to be precise with respect to the width of the conductor tracks in adjacent printed circuit board sections, for example the first printed circuit board section—more particularly 5-100%, preferably 10-75% or preferably 20-50% wider, in which printed circuit board section bending of the printed circuit board is required when assembling the latter in the target instrument. This can improve the electric signal transmission over the printed circuit board cable device. The spacing between the conductor tracks is substantially constant, at least in sections, and is more particularly between 50 µm and 350 µm, preferably between 100 µm and 250 µm or preferably between 150 µm and 200 µm.

A cover layer is preferably provided on at least one side or on both sides of the printed circuit board in order to protect the structures lying therebelow. Such a cover layer can have a polymer film or consist of the latter. The cover layer can have e.g. polyimide or a flexible solder resist or consist thereof. The cover layer is preferably connected, e.g. by lamination or adhesion, to the substrate in an inseparable fashion, i.e. it cannot be detached in a non-destructive manner.

It is also possible and preferable that a printed circuit board, at least in sections or over substantially its entire width—and preferably its length as well—, has more than one layer such that a plurality of substrates are arranged above one another as a stack. This affords the possibility of obtaining a higher line density (number of lines per cross-sectional area of the second printed circuit board section) in the second printed circuit board section in particular, while having an unchanged width dimension and an e.g. increased, preferably only slightly increased, height dimension. As a result of this, it is possible, if need be, to arrange more conductor tracks, e.g. double the number thereof, in the target region in the case of appropriately prescribed spatial conditions, for example in the second holding space for the second printed circuit board section.

The printed circuit board is provided with a number N of conductor tracks which, at least in the first printed circuit board section, preferably run parallel to one another in sections and preferably are arranged on the first side of the printed circuit board. By way of example, the number N emerges from the requirements of the electric apparatuses which should be connected to the printed circuit board cable device. By way of example, if an electric apparatus has a number of N sensors, it is preferable for at least (or precisely) N or N+1 conductor tracks to be provided for connecting the sensors to a second electric apparatus, e.g. a control apparatus and/or indicator apparatus (e.g. display), which is arranged at a distance from these sensors. The number N is preferably greater than three, five and particularly preferably greater than six, and is preferably between 6 and 99, preferably between 6 and 33, preferably between 6 and 17. In preferred exemplary embodiments, N=7 and N=15. However, N can also differ therefrom.

The printed circuit board preferably has a number m of through-holes, which make it possible to route one or more electric conductor tracks on the first side of the printed circuit board up to this through-hole and through this through-hole to the second side of the printed circuit board, where these one or more conductor tracks continue to run. To this end, an electric conductor is preferably arranged in a sleeve-like manner in this through-hole; this can, for example, be brought about simultaneously with the application of the conductor tracks. The through-holes can be made in the printed circuit board by boring, punching or other methods. The diameter of a through-hole is preferably between 0.2 mm and 1.0 mm, more particularly between 0.4 mm and 0.6 mm, but they can also be different.

The number m of through-holes is preferably selected such that any desired conductor track is routed from the one side of the printed circuit board to the other side of the printed circuit board through any through-hole. If a single conductor track is routed through each through-hole and if substantially half of the number N of conductor tracks in the first printed circuit board section should be routed from one side to the other side of the printed circuit board, the number of required through-holes is m=N/2 (i.e. ±1 if N is an odd number). The number m in the first and/or second and/or third printed circuit board section is preferably greater than one, two, three, four or five and particularly preferably greater than 6, and is preferably between 6 and 99, preferably between 6 and 33, between 6 and 17. In preferred exemplary embodiments, m=7 or m=15. However, m can also differ therefrom.

Depending on requirements, it is possible and preferable that one or more or all conductor tracks are already routed to the other side in the first printed circuit board section, more particularly routed from the first side of the printed circuit board to the second side of the printed circuit board. However, it is also possible that this only occurs in the second printed circuit board section. It is furthermore possible and preferable that one or more or all conductor tracks are respectively routed more than once from one side of the printed circuit board to the other side of the printed circuit board. The printed circuit board preferably (also) has a number of m=N/2 (i.e. ±1 if N is an odd number) through-holes in the third printed circuit board section, more particularly just like preferably also is the case in the first printed circuit board section.

In addition to the through-holes, the printed circuit board can have further openings or cut-outs which can also serve other purposes, for example which can make it possible to attach the printed circuit board in the laboratory sample instrument.

The printed circuit board is preferably elongate, i.e. the average length thereof is at least double the average width thereof. However, the printed circuit board can, for example, also be longer in order to be able to connect electric apparatuses which are spaced further apart. Stretched out in a planar fashion, the printed circuit board more particularly has a maximum length of between 20 and 500 mm, preferably between 50 and 400 mm, particularly preferably between 100 and 300 mm and very particularly preferably between 150 and 200 mm. Stretched out in a planar fashion, the printed circuit board preferably has a maximum width of between and 100 mm, preferably between 10 and 80 mm, preferably between 20 and 60 mm, and very particularly preferably between 30 and 40 mm.

The printed circuit board can have a substantially rectangular external outline or can, for example, have at least one curve or corner bend of e.g. 90° along its length, as a result of which it is possible to implement an outline that differs from the rectangular shape. The shape of the printed circuit board is not restricted and can ultimately be matched to the requirements, for example the available space, for example in the laboratory sample instrument.

The at least one first printed circuit board section preferably has a first width dimension and the at least one second printed circuit board section preferably has a second width dimension, the second width dimension being less than the first width dimension.

The width dimension is a measure for characterizing a width of a printed circuit board section. The width dimension of a printed circuit board section preferably denotes the width of the printed circuit board section, more particularly, in the case of a plurality of branch sections of a printed circuit board section, preferably the net width as the sum of the individual widths of all branch sections or preferably the width of an individual branch section or the net width of a plurality of branch sections. However, in respect of the definition of the invention, the width dimension of a printed circuit board section can alternatively or additionally also be defined such that it does not take into account the two edges that are formed by the distance between the two outer conductor track boundaries from the edge of the substrate of the printed circuit board. In this case, the maximum distance between the two outer conductor tracks of a conductor track bundle in a printed circuit board section is defined as the width dimension. A conductor track bundle can contain only conductor tracks arranged next to one another at the same height, or else denote conductor tracks arranged at different heights, for example ones which are attached to different sides of the printed circuit board. In this case, the height denotes the z-position in a Cartesian coordinate system if the printed circuit board is arranged in an x-y plane or even if, for example, the longitudinal axis of a more particularly elongate printed circuit board runs substantially parallel to the x-axis. The width dimension preferably denotes the average width (or net width) of the printed circuit board section (or of the at least one branch section) over the whole length of this printed circuit board section. However, it is also possible and preferable that the width dimension denotes the maximum or else the minimum width (or net width) of the printed circuit board section (or of the at least one branch section) with respect to the whole length of this printed circuit board section.

In the second printed circuit board section, the conductor tracks are preferably distributed over the first and second side of the board in substantially equal numbers (±1). As a result of this, it is possible that the second width dimension of the second printed circuit board section is substantially reduced compared to those sections of the printed circuit board, for example in the first printed circuit board section, in which the conductor tracks preferably all run or would run parallel next to one another. The advantage offered by this is that smaller spatial requirements are needed for holding the second printed circuit board section; in particular, less width, more particularly less net width, of this available space is needed for holding the printed circuit board cable device. As a result of this, the printed circuit board cable device can also electrically connect those regions in a laboratory sample instrument in which a bottleneck with little spatial availability makes a connection by conventional means either difficult or impossible.

By way of example, it is possible and preferable that the second width dimension is less than the first width dimension by a factor c, with c preferably lying between 0.2 and 0.9, preferably between 0.3 and 0.8, preferably between 0.4 and 0.77 and preferably between 0.5 and 0.7. However, c can also differ therefrom. The conductor tracks of the second printed circuit board section are preferably, over the greater part of the length of the second printed circuit board section or substantially along the whole length thereof, respectively arranged on the first and the second side of the board (or on the first or the second side of the board). The conductor tracks on the first and second side of the board of the second printed circuit board section are preferably arranged over at least 70% of the length of the second printed circuit board section, preferably over at least 85% of the length and particularly preferably over at least 95% of the length of the second printed circuit board section. However, it is also possible for one, more or all conductor tracks of the second printed circuit board section to change the side of the board a number of times.

It is possible and preferable that the second width dimension can be further reduced by arranging a plurality of printed circuit boards over one another. In the process, an arrangement with more than two plies, i.e. a multiple-ply printed circuit board arrangement is created in the second printed circuit board section or over a plurality of printed circuit board sections or else over the whole printed circuit board, which printed circuit board arrangement forms the printed circuit board cable device.

It is possible and preferable that the conductor tracks of the second printed circuit board section which are arranged at different heights are arranged offset with respect to one another, at least in sections or over their entire length, and do not intersect. This means that an imaginary plane perpendicular to the first side of the board and running through the conductor track and parallel to this conductor track does not cut any conductor track running parallel to said former conductor track at another height on the second side of the board. It is preferable for the conductor tracks, which are offset to one another and run parallel to one another at different heights, to have a spacing of, for example, a plurality of micrometers. As a result of this, the structures can be manufactured in a more reliable manner and have more constant electric properties. However, it is also possible that conductor tracks, which preferably run parallel to one another at different heights, in particular in the second printed circuit board section, intersect in part, to a lesser extent or completely in terms of the extent of their width.

In the first printed circuit board section, it is preferable for the majority of conductor tracks or all conductor tracks to be arranged on the first side of the board, at least in sections or over the greater part of the length of the first printed circuit board section or substantially along the whole length of the latter. Preferably, all conductor tracks are arranged on the first side of the board over 70% of the length, in particular 85% of the length and more particularly 95% of the length of the first printed circuit board section. As a result of this, it is possible, if necessary, to contact the conductor tracks towards their—preferably open—end in the direction of the end of the printed circuit board cable device on the same side, i.e. in the same fashion, and, for example, let them lead to a preferably provided amplified connection piece for a clamping plug.

One printed circuit board section, more particularly the second printed circuit board section, preferably has at least two and particularly preferably precisely two branch sections arranged next to one another, within which respectively a number of conductor tracks are arranged, with the sum of the width dimensions of the branch sections preferably corresponding to the second width dimension. An advantage emerging as a result of branching the printed circuit board into the plurality of branch sections in the second printed circuit board section is that the resulting printed circuit board cable device can also be arranged in those target instruments in which the second holding space for holding the second printed circuit board section is split into a plurality of sections, for example, as a result of a dividing structure of the target instrument dividing the second holding space into two or more sections. Branching the printed circuit board cable device and the plurality of branch sections in the second printed circuit board section can also be advantageous in other cases, for example if the connection between the printed circuit board cable device and the electric apparatus in the target region should only be implemented over a plurality of branch sections for geometric-structural arrangement reasons, for example in order to connect an electric apparatus, like e.g. a sensor apparatus, via the electric conductors. The exemplary embodiment shows such a case.

The preferably present third printed circuit board section preferably has a substantially annular or annular-segment-like design or an annular or annular-segment-like segment. In particular, if the target regions of the conductor tracks of the printed circuit board cable device, e.g. as contact points, are distributed equidistantly and concentrically on the annular surface, but not only in this case, provision is preferably made for the second printed circuit board section to have at least two or precisely two branch sections arranged next to one another and the third printed circuit board section to be substantially embodied as an annular ring, with, in particular, the first and second branch section respectively leading to a different half of the annular ring. The advantage emerging from this is that a first part of the conductor tracks can be routed over the one half of the ring and another part of the conductor tracks can be routed over the other half of the ring. As a result, spatial arrangement problems that emerge when distributing the conductor tracks on the annular ring are reduced or avoided. This advantage also emerges if the third printed circuit board section does not have an annular shape but rather has a different structure, for example if it is a continuation of the branch sections of the second printed circuit board section or has further branch points or bottlenecks.

Spatial arrangement problems when distributing the conductor tracks onto the annular surface or another structure of the third printed circuit board section can be further reduced by virtue of provision preferably also being made in the third printed circuit board section for part of the conductor tracks, at least in sections, to run on the first side of the board and another part of the conductor tracks, at least in sections, to run on the second side of the board. If necessary or desired, the conductor tracks on the second side of the board of the third printed circuit board section can be routed to the first side of the board by means of through-holes. Preferably a number $n1$ of conductor tracks run on the first side of the board in the third printed circuit board section and a number $n2$ of conductor tracks run on the second side of the board, with, preferably, $n1+n2=N$ (see above for the definition of "N") and with $n1$, $n2$ respectively in each case preferably lying between 2 and 99, between 5 and 50, between 8 and 32 or between 7 and 10.

It is also possible and preferable that a (first stage) branch section branches into at least two further second stage branch sections. It is then possible and preferable that the second stage branch sections have a smaller width dimension than the first stage branch section from which the second stage branch sections branch out. The smaller width dimension is preferably also achieved by virtue of the fact that at least one further substrate for conductor tracks is provided, which, in this second stage branch section, is arranged in a stacked manner with the first substrate for conductor tracks such that the conductor tracks of both substrates can, at different heights, run above one another or run offset to one another above one another. As a result of this, it is possible to subdivide the conductor tracks in the first printed circuit board section into a multiply branched region for example in the second printed circuit board section, wherein this multiply branched region in the second printed circuit board section can have a smaller width dimension than the first printed circuit board section. However, it is also possible that the width dimension thereof is substantially the same as, or greater than, that of the first printed circuit board section.

Provision is preferably made for the conductor tracks that run on the first side of the board in the third printed circuit board section respectively to lead to a contact electric contact (="contact") and provision is preferably also made for those conductor tracks that optionally run on the second side of the board in the third printed circuit board section to be routed to the first side of the board through holes in the printed circuit board and there respectively to lead to a contact, optionally by means of further conductor track sections on the first side of the board, with the contacts being arranged at a distance from one another on the first side of the board. However, it is also possible and preferable that target regions in the form of contacts are provided on both sides of the substrate.

A contact preferably consists of a first partial surface and a second partial surface, which are arranged at a distance from one another and can be electrically interconnected by a conductive contact element contacting the contact. The contact preferably consists of the same material as a conductor track of the printed circuit board but it can also have a different conductive material. It is preferable that precisely one conductor track of the printed circuit board is connected to each partial surface of the contact. Preferably at least one partial surface of the contact is connected to its own conductor track of the printed circuit board. In the process, it is more particularly possible for the second partial surfaces of a plurality of or of all contacts to be connected to one (or else several) common reference conductor tracks such that the first partial surfaces of the contacts can in each case be measured against the reference conductor track.

A contact furthermore preferably consists of first, electrically interconnected contact conductor tracks and of second, electrically interconnected contact conductor tracks, the first contact conductor tracks being electrically connected to a conductor track on the printed circuit board and the second contact conductor tracks being electrically connected to another conductor track on the printed circuit board and the first and second contact conductor tracks not being electrically connected. Here, provision is preferably made for the first and second contact conductor tracks to be arranged in meandering intercalated (interlocking) fashion without touching and to be electrically interconnectable by a conductive contact element contacting the contact. As a result of the meandering structure, the contacts are less susceptible to problems originating from height differences in the material of the contact or unevenness of the contacting contact element.

As a result of the contact by the contact element, the electric circuit between the first and second contact conductor tracks or between the two conductor tracks is closed, which can, for example, be detected by a drop in the circuit resistance. This is how contact sensors can be implemented, which for example detect a contact in a target region of a laboratory sample instrument and route the associated electric signal via the printed circuit board cable device and, in particular, through the narrow second holding space of the laboratory sample instrument to an electric apparatus, at a greater distance from the target region, in the laboratory sample instrument, for example a control apparatus, where this signal can be evaluated.

The laboratory sample instrument according to the invention can be such an instrument in which liquid or gel-like laboratory samples are worked on, processed, held, emitted, transported or even only examined, for example examined by optical and/or electric or electromagnetic means. The laboratory sample instrument preferably is an instrument for holding and dispensing and/or metering a liquid laboratory sample (metering device). The laboratory sample instrument is preferably embodied as pipetting device, to be precise either as pipette or as a repeater pipette (dispenser). The laboratory sample instrument can be a manual laboratory sample instrument, i.e. operable by hand, handheld, and mobile, or else it can be a stationary, non-mobile instrument in which the processes of taking up and emitting the laboratory samples are preferably automatic. Hence, the laboratory sample instrument can also be part of a more comprehensive robot system or part of a laboratory management system (LMS).

The laboratory sample instrument according to the invention, more particularly the dispenser, has a cable holding space in which a printed circuit board cable device is arranged, the cable holding space being subdivided into at least one first, second and third holding space, with the first printed circuit board section being arranged in the first holding space, the second being arranged in the second holding space and the third being arranged in the third holding space, the second holding space, when considered perpendicular to the printed circuit board, having a smaller cross-sectional area than the first holding space. As a result of using the printed circuit board cable device, it is possible to make a laboratory sample instrument according to the invention more compact. This particularly relates to the second and optionally also the third holding space with the second and third printed circuit board sections, respectively. As a result of the compact design of the laboratory sample instrument, the production thereof firstly becomes more cost effective and secondly, such a laboratory sample instrument can be used in a more flexible manner because the space saved as a result of the compact design improves the overview or is available for other purposes.

The laboratory sample instrument preferably has a first, second and third instrument section, in which respectively the first, second and third holding spaces are arranged, the printed circuit board cable device bringing about an electric connection between an electric apparatus arranged in the first instrument section and a second electric apparatus, more particularly a sensor apparatus, arranged in the third instrument section, with contacts preferably being provided at the ends of the conductor tracks in the third printed circuit board section, which contacts have two spatially separated contact regions and are respectively associated with a sensor of the sensor apparatus by virtue of the closing of an electric circuit being detectable by a conductive contact element simultaneously contacting the two contact regions of a contact.

The laboratory sample instrument preferably has a main body which preferably has an elongate shape, that is to say the length of the main body is at least double the width and depth thereof. The elongate body preferably extends along a length axis of the laboratory sample instrument. At one end, the main body can have an end face which, in the case of an elongate body, is less than the side faces. The end face can be designed for mounting a means in which the laboratory sample is taken up, e.g. an optical objective, an electric probe or a syringe or pipette tip or the like. The end face can be arranged substantially perpendicular to the length axis.

The printed circuit board cable device is preferably arranged within the main body and preferably arranged such that the third printed circuit board section is arranged closer to the end face than the first printed circuit board section, which preferably extends in the direction of the interior of the main body. The third printed circuit board section is preferably arranged parallel to the end face or another side of the main body. As a result, the surface of the third printed circuit board section can be used particularly easily for the interaction with further components outside of the main body, for example as sensor field for identifying separate means which are connected to the laboratory sample instrument and in which the laboratory sample is held. As a result of the compactness of the printed circuit board cable device, the laboratory sample instrument according to the invention can have a more compact design, particularly in the region of such an end face.

Preferably, the laboratory sample instrument has an electric apparatus, for example a sensor apparatus, in particular for identifying the utilized pipette tip. The electric apparatus is preferably arranged inside the laboratory sample instrument, preferably in the third instrument section. Preferably at least a part of the electric apparatus is formed by the printed circuit board cable device, in particular formed by the third printed circuit board section and/or a part of the second printed circuit board section.

Preferably, the laboratory sample instrument has at least one auxiliary device, which is arranged in the second instrument section and/or the third instrument section. The auxiliary device can be a mounting device. The mounting device can be configured for reversibly mounting an external device, in particular a sample container, to the laboratory sample instrument preferably a pipette tip or a syringe, e.g. in case that the laboratory sample instrument is a dispenser. The mounting device can comprise a clamp mechanism, in particular a snap-in joint. Preferably, the snap-in joint comprises at least two holding members, which are in particular spring mounted to the laboratory sample instrument, in particular to a base body or the housing of the laboratory sample instrument. Preferably, the mounting device is configured to let the external device be manually mounted and/or unmounted, in particular, be manually locked and/or unlocked. Preferably, the clamp mechanism has at least two clamp members mounted in opposite to each other, arranged on opposing sides of the length axis of the laboratory sample instrument.

Preferably, the electric apparatus has a movable part, in particular a contact socket. The movable part can be configured to be movable in the direction parallel to the length axis of the laboratory sample instrument, and can be configured to be unmovable with respect to the other directions, in particular by means of a guiding device, which guides the movement of the movable part. The contact socket is adapted to be contacted by the external device, if the same is mounted to laboratory sample instrument. Preferably, the contact socket is spring mounted to the laboratory sample instrument, in particular directly or indirectly to a base body or the housing of the laboratory sample instrument.

Preferably, the auxiliary device is a holding device: preferably, the laboratory sample instrument has a holding device, which holds the movable part in connection with the laboratory sample instrument and which preferably is arranged in the second instrument section and/or the third instrument section, preferably in combination with the mounting device. The holding device, preferably, is mounted to the laboratory sample instrument, in particular directly or indirectly to a base body or the housing of the laboratory sample instrument. The holding device can be configured to form a block device which blocks the movement of the movable part. Preferably, the holding device has two holding members mounted in opposite to each other, arranged on opposing sides of the length axis of the laboratory sample instrument.

The auxiliary device, in particular the holding device and/or the mounting device are preferably arranged in the second and/or third instrument section. Therefore, the available space is reduced in the second and/or third instrument section. In this situation, it is preferred to reduce the space for the cable holding space, which is arranged in the second and/or third instrument section, in particular to reduce the space for the second and third cable holding space. Even under such limited space conditions, the printed circuit board cable device, in particular the second and/or third printed circuit board section, can be arranged in the second and/or third instrument section, because in the second printed circuit board section, at least one conductor track is arranged on the first side of the board and at least one conductor track is arranged on the second side of the board. This way, the problems of space limitation are overcome.

It is in particular advantageous to provide at least two branch sections of the second printed circuit board section. It is preferred, that between two of the branch sections, a part of the auxiliary device is arranged, in particular, a part of the holding device is arranged. This way, the problems of space limitation are further reduced. In this case, the part of the auxiliary device or, respectively, the holding device, which is arranged between the branch sections, is forming the dividing structure, mentioned before, of the target instrument dividing the second holding space into two or more sections.

The invention furthermore relates to a method for producing the laboratory sample instrument according to the invention, comprising the following steps: providing the printed circuit board cable device;—arranging the printed circuit board cable device in a cable holding space of the laboratory sample instrument, more particularly bending part of the printed circuit board cable device, more particularly the third printed circuit board section.

The method can comprise steps for producing the printed circuit board cable device, comprising the following steps:— providing a substrate;—applying the conductor tracks on the substrate, more particularly in the first, second and third printed circuit board section, more particularly applying conductor tracks on both sides, at least in the second printed circuit board section, more particularly manufacturing of at least some of the conductor tracks or all conductor tracks in integral fashion;—preferably: providing an electrically conductive sleeve element, more particularly as component of a conductor track, with the sleeve element preferably forming the transition of a conductor track from one side of the board to the other side of the board and preferably being arranged in a through-hole (130; 131) of the printed circuit board.

Further preferred embodiments of the laboratory sample instrument according to the invention emerge from the following description of the exemplary embodiments in conjunction with the figures. The same reference signs denote substantially equivalent components.

FIGS. 1*a*, 1*b* and 1*c* show a schematic plan view of in each case a different exemplary embodiment of the printed circuit board cable device of an embodiment of the laboratory sample instrument according to the invention.

FIG. 2 shows a schematic partial view of a further exemplary embodiment of the printed circuit board cable device of an embodiment of the laboratory sample instrument according to the invention.

FIGS. 3a and 3b respectively show a cross section through the first printed circuit board section of different exemplary embodiments of the printed circuit board cable device of an embodiment of the laboratory sample instrument according to the invention.

FIGS. 4a and 4b respectively show a cross section through the second printed circuit board section of different exemplary embodiments of the printed circuit board cable device of an embodiment of the laboratory sample instrument according to the invention.

FIGS. 5a, 5b and 5c respectively show a cross section through the second printed circuit board section of different exemplary embodiments of the printed circuit board cable device of an embodiment of the laboratory sample instrument according to the invention.

FIG. 6a shows a plan view of an exemplary embodiment of the printed circuit board cable device of an embodiment of the laboratory sample instrument according to the invention.

FIG. 6b shows the view from below of the printed circuit board cable device from FIG. 6a.

FIG. 6c shows a plan view of the substrate of the printed circuit board cable device from FIG. 6a, with the through-holes being visible.

FIG. 7a shows a schematic front-on view of a laboratory sample instrument from the prior art.

FIG. 7b shows a schematic side view of the embodiment of the laboratory sample instrument from FIG. 7a.

FIG. 9b shows a plan view of a detail of the printed circuit board cable device from FIG. 9a.

FIG. 9c shows a view from below of a detail of the printed circuit board cable device from FIG. 9a.

FIG. 10a shows a part of a mounting device for mounting a dispenser syringe of a preferred embodiment of the laboratory sample instrument according to the invention, in a first position, where the dispenser syringe is not mounted.

FIG. 10b shows the mounting device of FIG. 10a, where the dispenser syringe is mounted.

Figure 8:
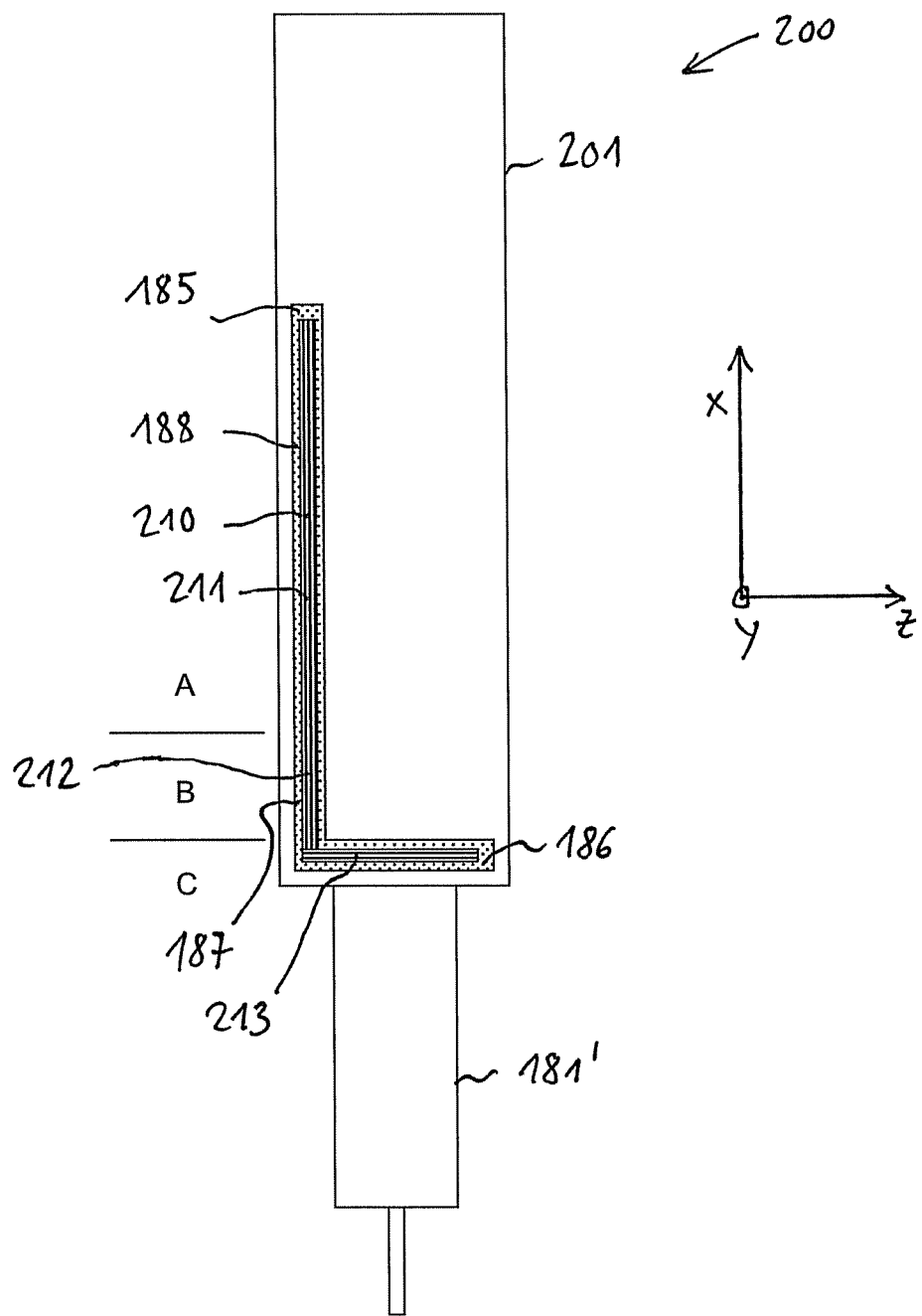
FIG. 8 shows a schematic side view of an embodiment of a laboratory sample instrument according to the invention.

FIG. 1a schematically shows a plan view of a printed circuit board cable device 1 of an embodiment of the laboratory sample instrument according to the invention, as per a first exemplary embodiment. The printed circuit board cable device 1 has an elongate flexible printed circuit board 2. The base material of the electrically insulating, flexible substrate of this printed circuit board can for example be polyimide. Conductor tracks (3, 4, 5, 6) run over substantially the whole length of the printed circuit board 2 on the visible first side of the board of the printed circuit board 2. The outlines of the bundle of the conductor tracks, which run substantially parallel to one another in most sections of the printed circuit board, are only shown schematically in FIG. 1a. The two dotted, horizontal lines which cross all FIGS. 1a, 1b and 1c, mark the three regions A, B, C. The respectively first printed circuit board section is situated in region A, the second printed circuit board section is situated in region B and the third printed circuit board section is situated in region C.

In the first printed circuit board section A, the printed circuit board 2 has a region 8 with through-holes. The bundle 3 of the conductor tracks running parallel in section A branches in the vicinity of the region 8, with the two illustrated branch sections 4, 4' continuing to run on the first side of the board in the region A. By contrast, respectively half of the conductor tracks from the centre of the conductor-track bundle 3 are routed to the second side of the board through an electrically conductive through-hole in the region 8 and are routed on such that, respectively for each branch section 4, 4', there is a complementary partial bundle of conductor tracks (not visible) which runs below the branch sections 4, 4'. In front of the transition into the second printed circuit board section B, all conductor tracks change direction and once again run parallel to the first bundle 3 of conductor tracks in the first printed circuit board section.

In the second printed circuit board section B, a partial bundle 5 of conductor tracks run parallel to one another on the first side of the board and a partial bundle complementary thereto (not illustrated) runs on the second side of the board below the partial bundle 5; this is the case in each branch section. The partial bundle 5 of conductor tracks (and the partial bundle complementary thereto) in each case extends into the third printed circuit board section C. There, each conductor track preferably ends in an open end, which is available for connection to an electric apparatus, for example a sensor apparatus.

The second printed circuit board section B has a smaller width dimension than the first printed circuit board section A because the average net width of the printed circuit board in the second printed circuit board section B, i.e. the average width of the branch sections of the printed circuit board in the region B, is less than the average width of the first printed circuit board section A. The same also applies analogously here to the width or net width of the cable bundles in the regions B and A. The width dimension of the third printed circuit board section C is in this case substantially equal to the one in the region B. As a result of transferring some of the conductor tracks 3 onto the second side of the board it is thus possible to reduce the width dimension of the printed circuit board in the region B, and so the printed circuit board requires less holding space in this region B. As a result of the conductor tracks being arranged as running substantially over one another in the region B, the width (or net width) of the cable bundles 5 (also taking into account the cable bundles running therebelow, i.e. those referred to as complementary) is furthermore also reduced. As a result, it is easier to route the conductor tracks through bottlenecks. The width dimension will furthermore be explained in more detail in conjunction with FIGS. 2 to 3b.

FIG. 1b shows a schematic plan view of the printed circuit board cable device 10 as per another exemplary embodiment of the laboratory sample instrument according to the invention. In regions A and B, the printed circuit board cable device 10 or the printed circuit board 12 has substantially the same fork-like structure of the printed circuit board cable device 1 from FIG. 1a; however, it has a different embodiment in the third printed circuit board section C. The embodiment has an annular design in FIG. 1b. In this region, starting from respectively one branch section in region B, the conductor tracks (not shown) respectively run in one half of the ring, to be precise both on the first side of the board and on the second side of the board. In the region of the transition from region B to region C, each partial bundle of conductor tracks on each side of the board can once again branch such that respectively one partial bundle runs in the direction of the axis of symmetry of the printed circuit board and another partial bundle runs away from the axis of symmetry. The open ends of each conductor track are arranged in the region of the ring and can for example be embodied as contacts and can for example be part of a sensor apparatus.

FIG. 1c shows a schematic plan view of the printed circuit board cable device 20 as per another exemplary embodiment of the laboratory sample instrument according to the invention. In this case, the printed circuit board 22 branches into three branch sections in the second printed circuit board section B. In each branch there are conductor tracks running substantially over one another both on the first side of the board and on the second side of the board. The minimum net width of the branch sections in the second printed circuit board section B is less than the minimum width of the first printed circuit board section A, and so the second width dimension is less than the first width dimension.

FIG. 2 shows a schematic partial plan view of the printed circuit board cable device 30 as per another exemplary embodiment of the laboratory sample instrument according to the invention. The conductor tracks (33, 35, 36) run in each printed circuit board section A, B and C, with once again only the outlines of the bundles of conductor tracks being shown, substantially parallel at least in sections. In the region of the bundle 33, this results in an arrangement which can for example have a cross section (perpendicular to the plane of the drawing) along the dashed line E1 which corresponds to the cross section shown in FIG. 3a.

The printed circuit board 32 of the printed circuit board cable device 30 does not have a branching, but rather tapers in a step-like or continuous fashion, starting from the first printed circuit board section A, over the second printed circuit board section B, to the third printed circuit board section C. On the one hand, this is possible because the conductor tracks in the second printed circuit board section B run on both the first and the second side of the board and are furthermore in particular arranged as running substantially over one another. In the region of the bundle 35, this results in a stack of conductor tracks or a multiple-ply (in this case two-ply) printed circuit board section, which, along the dashed line E2, can for example have a cross section which corresponds to the cross section shown in FIG. 4a.

Moreover, the bundle 36 of conductor tracks is arranged in more than two plies in the third printed circuit board section C by virtue of the fact that a further substrate is arranged there. A stack of conductor tracks or a multiple-ply (in this case three-ply) printed circuit board section emerges in the region of the bundle 36, which printed circuit board section, along the dashed line E3, can for example have a cross section which corresponds to the cross section shown in FIG. 5a or 5b.

The second width dimension of the second printed circuit board section B is less than the first width dimension of the first printed circuit board section A because the minimal width B2 of the second printed circuit board section B is less than the minimum width B1 of the first printed circuit board section A. Furthermore, the minimum width b2 of the bundle 35 of the conductor tracks of the second printed circuit board section B is also less than the minimum width b1 of the bundle 33 of the conductor tracks of the first printed circuit board section A. As a result of the three-ply arrangement of the conductor tracks 36 in the third printed circuit board section C, the third width dimension is less than the second width dimension in this case. Such a printed circuit board cable device can also be used in those instruments in which the corresponding cable holding space for holding the second and third printed circuit board section only provides a smaller width.

FIG. 3a shows the cross section of a printed circuit board cable device 40 as per a further exemplary embodiment of the laboratory sample instrument according to the invention; to be precise, it shows the cross section through the first printed circuit board section thereof. The printed circuit board 42 has a substrate 43 made of polyimide, on which 15 metallic conductor tracks 46 are arranged running parallel to one another. Adjacent conductor tracks are spaced apart by a constant distance that is greater than the width of a conductor track. The upper, first side of the board of the printed circuit board 42 is protected by a cover layer 45 made of plastic, which forms a continuous, partly transparent protective film over the upper side of the substrate 43 and over the conductor tracks 46. Correspondingly, the lower, second side of the board is covered by a similar cover layer 44. The cross section can be associated with a width dimension B1, which is defined by the width of the printed circuit board 42 of the cross section, and furthermore it can be associated with a similar width dimension b1, which is defined by the width of the cable bundle of the cross section, formed by the individual conductor tracks 46. Independently of the precise number of conductor tracks, it is preferable for a printed circuit board cable device of an embodiment of the laboratory sample instrument according to the invention to be able to have such a cross section in the first printed circuit board section.

FIG. 3b shows the cross section of a printed circuit board cable device 50 as per a further exemplary embodiment of the laboratory sample instrument according to the invention; to be precise, as in FIG. 3a, it shows the cross section through the first printed circuit board section. In this case, the first printed circuit board section of the printed circuit board 52 of the printed circuit board cable device 50 has a branched design, and has a first branch section 52a and 52b. Branch section 52a carries a first cable bundle consisting of seven conductor tracks 56 and branch section 52b carries a second cable bundle consisting of eight conductor tracks 56. Beyond this, the branch sections substantially have the same design and have a substrate (53a; 53b) and an upper (55a; 55b) and lower cover layer (54a; 54b). The width dimension of this first printed circuit board section can be specified as a net width. The net width is the sum of the width dimensions of the two branch sections, i.e., for example, the sum B1_1+B1_2 of the widths of the two branch sections of this cross section or the sum b1_1+b1_2 of the widths of the two cable bundles of this cross section. It is also possible that a first printed circuit board section is designed such that it has both the cross section as per FIG. 3a and the cross section as per FIG. 3b. Furthermore, in general, it is also possible in the case of a printed circuit board cable device that a number nx of conductor tracks already runs (or else: does not run) on the second side of the board in the first printed circuit board section, i.e. wherein provision is preferably made in each case for nx<7, particularly preferably for nx<4 and more preferably for nx<2.

FIGS. 4a and 4b respectively show a cross section through the second printed circuit board section of different exemplary embodiments of the printed circuit board cable device (60; 70) of an embodiment of the laboratory sample instrument according to the invention. Like in the exemplary embodiment for the cross section of the first printed circuit board section shown in FIGS. 3a and 3b, the second printed circuit board section can also have a branched design, as shown in FIG. 4b, or, at least in sections, not have a branched design, in accordance with the cross section in FIG. 4a. In the second printed circuit board section, the printed circuit board cable device 60 has a printed circuit board 62 which is not branched and in which, above the substrate 63, eight conductor tracks 66 are arranged parallel to and spaced apart equidistantly from one another and in which, below the substrate 63, seven conductor tracks 67 are arranged spaced apart equidistantly from one another. Thus, overall, 15 conductor tracks are visible. Here, the upper and lower conductor tracks of the first side of the board and of the second side of the board are arranged substantially offset to one another on the substrate 63, i.e. no x-z plane of the displayed Cartesian coordinate system intersects (at least in the region of this cross section) both an upper conductor track 66 and a lower conductor track 67. Each side of the board is protected by a cover layer (64; 65). The width dimension B2 of this second printed circuit board section is e.g. less than the width dimension B1 of the first printed circuit board section shown in FIG. 3a.

FIG. 4b shows the printed circuit board 72, which has a first branch section 72a and a second branch section 72b. The branch section 72a has eight conductor tracks, namely four conductor tracks 76a on the upper first side of the board and four conductor tracks 77a on the lower second side of the board. By contrast, the branch section 72b has seven conductor tracks, namely four conductor tracks 76b on the first side of the board and three conductor tracks 77b on the second side of the board. Respectively one cover layer (75a; 75b; 74a; 74b) is provided on each side of the board. By way of example, the width dimension of the second printed circuit board section shown in FIGS. 4a and 4b is respectively for example less than the width dimension of the first printed circuit board section shown in FIG. 3a or 3b, since B2 or the net width B2_1+B2_2 is respectively less than B1 or B1_1+B_12.

FIGS. 5a, 5b and 5c respectively show a cross section through the second printed circuit board section of different exemplary embodiments of the printed circuit board cable device (80; 80'; 90) of an embodiment of the laboratory sample instrument according to the invention. FIGS. 5a and 5b respectively show a multiple-ply design of the printed circuit board 82 in the second printed circuit board section, which respectively has two substrates (83a; 83b), which are separated by an intermediate layer which may, for example, consist of a polyimide. As a result of this, it is possible, as shown, to provide the conductor tracks 86b (in this case: three conductor tracks) on the lower side of the upper substrate 83a and, at the same time, provide conductor tracks 87b (in this case: four conductor tracks) on the upper side of the lower substrate 83b. Naturally one of the two plies of conductor tracks (86b; 87b) arranged in the interior of the printed circuit board can also be omitted. On the upper side of the upper substrate 83a there are four conductor tracks 86 and on the lower side of the lower substrate 83b there are likewise four conductor tracks. In FIG. 5a, the conductor tracks 86 and 86b as well as 86b and 87b are respectively arranged offset with respect to one another while the conductor tracks 86, 87b and 87 run arranged directly over one another. However, it is also possible to arrange the various plies of the conductor tracks offset to one another in another fashion, for example by virtue of the fact that, preferably, the conductor tracks on the upper and lower side of the substrate are in each case preferably respectively arranged offset to one another, as shown in FIG. 5b. The second width dimension of such an arrangement of the second printed circuit board section can be even further reduced compared to the two-ply printed circuit board arrangement for example shown in FIG. 4a or 4b.

FIG. 5c shows an example of a second printed circuit board section, in which the printed circuit board 92 has three substrates 93a, 93b and 93c, which are respectively separated by an intermediate layer 98, 98' and enclosed on the outside by cover layers 95, 95'. The second width dimension of such a six-ply arrangement of the second printed circuit board section can be even further reduced compared to the four-ply printed circuit board arrangement for example shown in FIG. 5a or 5b.

The exemplary embodiments from FIGS. 4a, 4b and 3a, 3b, and also 5a, 5b and 5c can naturally be combined in order to obtain a desired printed circuit board cable device of an embodiment of the laboratory sample instrument according to the invention.

In a plan view, FIG. 6a shows the substantially planar printed circuit board cable device 100 as per a preferred embodiment of the laboratory sample instrument according to the invention. Preferred proportions in the x-y plane can, to the extent that this is possible, optionally be taken from FIGS. 6a, 6b and 6c. The printed circuit board cable device 100 has a substantially elongate form, the maximum width of which (respectively from the outmost edge to edge in the y-direction) is approximately 35 mm and the maximum length of which (respectively from the outmost edge to edge in the x-direction) is approximately 170 mm. The maximum height (respectively from the outmost edge to edge in the z-direction) is approximately 0.2 mm. The printed circuit board 102 has a first printed circuit board section A, a second printed circuit board section B and a third printed circuit board section C. The first printed circuit board section is substantially composed of a first, substantially U-shaped segment (104, 106, 107, 108) in the region A1 and an elongate, rectangular second segment 103 in the region A2, situated between said first segment (104, 106, 107, 108) and the second printed circuit board section (in the region B). The segment 103 is suitable for bridging a predetermined distance (in this case: approximately 60 mm) along the longitudinal side of an elongate main body of a laboratory sample instrument. The segment 103 in A2 can be affixed in a laboratory sample instrument by means of the through-holes 116, for example by a screw connection, as a result of which this segment is mechanically secured, in particular against bending and slippage. As a result of this, there is a lower mechanical load on the conductive sleeve in particular, which preferably forms the transition of a conductor track from one side of the board to the other side of the board and is arranged in the through-hole (130; 131). The substantially rectangular and elongate segment 104, adjoining the segment A2, extends from the corner connection 105 substantially at right angles to the segment 103. The segment 104 is suitable for being arranged in a curved manner (radius for example between 10 mm and 30 mm), as a result of which it can partly grasp around those components in the main body of the laboratory sample instrument which are arranged within the radius of curvature. Segment 106 is embodied as once again running substantially along the x-axis, but offset with respect to the segment 103, and bridges a further distance until the rectangular curvature region 109 leads to the segment 107, which runs substantially parallel to but is shorter than segment 104. The segment 107 is completed by a strengthened region 108 with a greater thickness, in which the conductor tracks in the form of electric contact points are exposed. The segment 108 can thus be used as plug region for plugging into a female plug in any electronic apparatus, for example the control apparatus of a laboratory instrument.

The second printed circuit board section of the printed circuit board cable device 100 in the region B has a first branch section 110 and a second branch section 111. Both branch sections are separated by a cavity. The advantage offered by this is that the printed circuit board cable device 100 can also be arranged in those laboratory sample instruments according to the invention in which the second holding space for holding the second printed circuit board section of the printed circuit board cable device 100 is occupied by arbitrary components and is unavailable to the printed circuit board cable device. Secondly, a laboratory sample instrument according to the invention with such a printed circuit board cable device can have a more compact construction and a more flexible design because the second printed circuit board section has a smaller width dimension than the first printed circuit board section. These advantages substantially apply to all printed circuit board cable devices of embodiments of the laboratory sample instrument according to the invention within the scope of the present description of the invention.

In the connection region 112 of the second printed circuit board section to the third printed circuit board section, the printed circuit board 102 is designed to be bent. This feature substantially applies to all printed circuit board cable devices of embodiments of the laboratory sample instrument according to the invention within the scope of the present description of the invention. By means of this curvature, the third printed circuit board section can preferably be arranged bent by 90° with respect to the second printed circuit board section. In the laboratory sample instrument according to the invention, a printed circuit board cable device is preferably arranged such that the third printed circuit board section is arranged bent by an angle a with respect to the first and/or the second printed circuit board section, wherein, preferably, a=90° (including ±5°) or 70<a<120° applies or a is different. In order to stabilize the curvature, curvature-aid sections 113 can be provided, which extend in the region of the transition between the second and the third printed circuit board section in the predetermined curvature region. In the printed circuit board cable device 100, the curvature-aid sections 113 are embodied as elongate metal elements, which together preferably have a larger overall cross section than all conductor tracks in the curvature region of the printed circuit board. The curvature of the sections 113 is preferably formed to prevent the elastic restoration force of the partly elastic and flexible printed circuit board 102 made of Kapton® from removing the curvature again after the printed circuit board was curved. This can prevent excessive stress on the conductor tracks in the region of the curvature.

The third printed circuit board section in the region C adjoins the second printed circuit board section in the region B. The third printed circuit board section has a substantially annular design by virtue of the fact that an annular section 114 is provided. The annular section 114 has a first half of the ring 114a, which is situated below the dashed line E4 in FIG. 6a, and furthermore a second half of the ring 114b, which is situated above the dashed line E4. The annular section 114 furthermore has four corner flanges 115, which are situated in the plane of the ring and respectively have one bore 116, by means of which the third printed circuit board section can for example be assembled in the interior of a laboratory sample instrument.

The printed circuit board cable device 100 has 15 conductor tracks in the first and second printed circuit board section. Said conductor tracks substantially almost always run parallel in the essential segments, at least parallel in a partial-bundle-like fashion. In the region of the corner bend 105, the main bundle 120 of in total 15 conductor tracks arranged substantially equidistantly from one another separates into a first partial bundle 121 consisting of eight conductor tracks arranged equidistantly from one another and into a second partial bundle 122 consisting of seven conductor tracks arranged equidistantly from one another. The region A3 is furthermore provided in the segment A2 of the first printed circuit board section. In this region A3, substantially half of the conductor tracks of the first and the second partial bundle 121, 122 respectively change from the first side of the board (visible) to the second side of the board (not visible). In the case of the first partial bundle 121, these are four conductor tracks 121b and, in the case of the second partial bundle 122, these are three conductor tracks 122b (see FIG. 6b). The total of seven through-holes 130 of the printed circuit board in the region A3, along which the conductor tracks respectively change side, are not visible in FIGS. 6a and 6b. From the region A3 onwards, only the upper four conductor tracks 121a of the first partial bundle 121 and the upper four conductor tracks of the second partial bundle 122 are still visible in FIG. 6a.

In the region C of the third printed circuit board section, the conductor tracks of the first partial bundle 121 substantially all lead to the first half of the ring 114a and the conductor tracks of the second partial bundle 122 substantially all lead to the second half of the ring 114b of the annular section 114. This design in particular affords the possibility of embodying the two arms of the halves of the ring to be relatively narrow, as a result of which, furthermore, the advantage arises that the third printed circuit board section in a laboratory sample instrument requires a smaller holding space. As a result of this, a laboratory sample instrument according to the invention, equipped thus with a printed circuit board cable device, can have a more flexible design. Furthermore, this embodiment more particularly renders it possible to route a comparatively large number of conductor tracks from the second printed circuit board section to the third printed circuit board section, without the relatively small second width dimension of the second printed circuit board section becoming a problem. As a result of this, it is possible to implement a more complex electronic apparatus, for example a scanning apparatus with a relatively large number NA=14 of scanning points.

In the region B of the second printed circuit board section, the conductor tracks substantially run as shown in the exemplary embodiment of FIG. 4b. In the region 106 of the first printed circuit board section, the conductor tracks substantially run as shown in the exemplary embodiment of FIG. 3a. In the region 106 of the first printed circuit board section, the conductor tracks substantially run as shown in the exemplary embodiment of FIG. 3a. In the region 103 of the first printed circuit board section, the conductor tracks substantially run as shown in the exemplary embodiment of FIG. 3b.

FIG. 6b shows the underside of the printed circuit board cable device 100 after a rotation about 180°. As shown in FIG. 6b, the lower conductor tracks of the first and second partial bundles 121b, 122b also run substantially on the second side of the board, i.e. on the underside of the printed circuit board 102, in the annular section. In FIG. 6c, the printed circuit board 102 is displayed without applied conductor tracks. The comparison of FIGS. 6a, 6b and 6c shows at which positions, specifically the through-holes 131 of the annular section, the lower conductor tracks of the first and second partial bundles 121b, 122b are routed back onto the first side of the board, where they either lead into a region of a contact 140 or are routed by means of a further conductor track section (barely visible) to a region of a contact 140.

Overall, a total of NA=14 contacts 140 are provided, to which respectively at least one of the 15 conductor tracks of the conductor track bundle 120 leads. One contact is embodied as contact sensor field of a touch sensor, which is provided as part of a scanning apparatus of a laboratory instrument, for example of the laboratory instrument according to the invention, which, for example, is described in the exemplary embodiment of FIG. 8. A contact 140 has a first contact region and a second contact region, wherein both contact regions are spaced from one another and are therefore electrically separated. The two contact regions can be electrically connected by means of a separate contact element, which can be a graphite disk; this connection can be detected as a drop in the electric resistance over the corresponding conductor tracks. Such a contact element can be part of a scanning apparatus of a laboratory instrument according to the invention, in which the printed circuit board cable device is arranged. Each contact region has a multiply wound or branched, delicate line which intercalates with the complementary contact region which has an analogous design. As a result of this, the reliability of the contacting is improved.

Figure 9A:
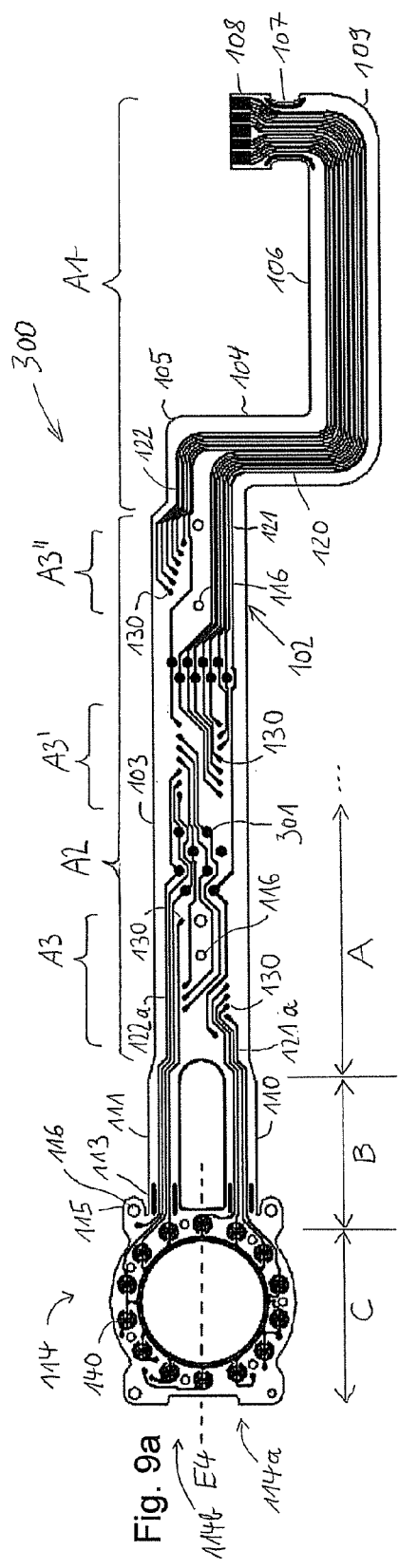
FIG. 9a shows a plan view of a further exemplary embodiment of the printed circuit board cable device of an embodiment of the laboratory sample instrument according to the invention.
Figure 9B:
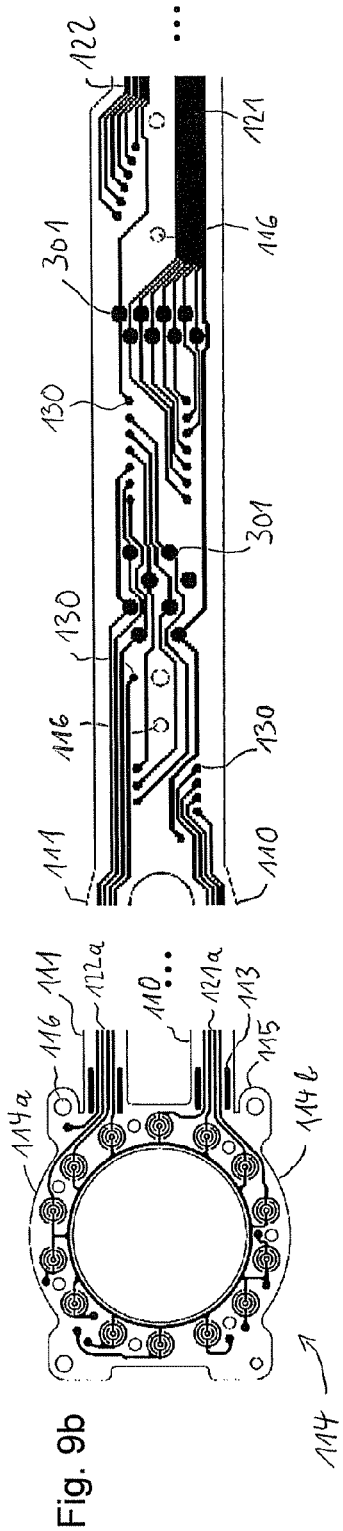
Figure 9C:
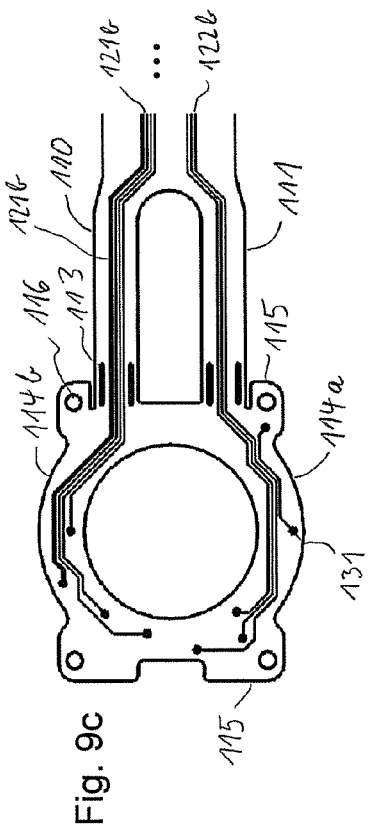

FIG. 9a shows a plan view of the printed circuit board cable device 300, which substantially has the same functional components as the printed circuit board cable device 100, with reference being made to the description thereof. Substantially equivalent components of both printed circuit board cable devices 100 and 300 are therefore denoted by the same reference signs. In the printed circuit board cable device 300, the segment 103 or A2 of the first printed circuit board section A has a number of subsections A3, A3' and A3", which serve the purpose of ensuring that every conductor track of the two conductor track bundles 121, 122 is routed at least once from the first side of the board to the second side of the board or from the second side of the board to the first side of the board. As a result of the fact that a plurality of mutually separated subsections A3, A3' and A3" of the printed circuit board 102 are used for this purpose, there is enough space for arranging through-holes 130 and further structures in the segment 103. In the present case, such a further structure is the arrangement of test contact points 301 made of conductive material, which can be contacted by means of an external test device in order to test the functionality of the printed circuit board cable device. The production of a reliable printed circuit board cable device is simplified by these test contact points. FIG. 9b shows a plan view of a detail of the printed circuit board cable device from FIG. 9a. FIG. 9c shows a view from below of a detail of the printed circuit board cable device from FIG. 9a.

FIG. 7a shows a schematic front-on view of the outlines of a laboratory sample instrument from the prior art. The laboratory sample instrument is the manual dispenser "Multipette® Xstream" by Eppendorf AG, Germany, commercially available in 2011. From top to bottom, the manual dispenser 180 has such a profile that it tapers in the direction of a laboratory sample vessel 182. The outlines of the manual dispenser are partly due to technical reasons and partly determined by the design concept of Eppendorf AG, Germany. The sample can be taken up or emitted in metered fashion by means of the syringe 181, which is a disposable article. By way of example, the syringe 181 holds 10 ml sample volume and is likewise commercially available in 2011 as a compatible accessory by Eppendorf AG, Germany. The syringe 181 cannot be seen in its entirety in FIG. 7a because it is partly arranged in the interior of the main body 180 of the manual dispenser.

FIG. 7b shows a schematic side view of the laboratory sample instrument from FIG. 7a. In this case, the syringe 181 which in region C is formed by the flange section 181a, by the encoding profile flange 181b and by the piston coupling part 181c is illustrated schematically and in its entirety. The encoding profile on the end face of the encoding profile flange 181b renders it possible for the manual dispenser 180, with the aid of a scanning apparatus, to identify automatically the type of the syringe coupled to the instrument.

The main body 180 of the manual dispenser has a cable holding space 185, 186, which, particularly in the region B, is spatially very restricted as a result of the design requirements of housing the coupling mechanism for holding the syringe and the scanning apparatus. Since the scanning apparatus uses its touch sensors to scan the end face of the encoding profile flange 181b, the cable holding space 186 is arranged perpendicularly to the longitudinal axis of the laboratory sample instrument. Accordingly, the third printed circuit board section, which is arranged in the region 10, should be angled at approximately 90°, preferably between 80° and 100° and particularly preferably between 88° and 92°, with respect to the longitudinal axis, in the direction of which the first and the second printed circuit board section lie.

FIG. 8 shows a schematic side view of a laboratory sample instrument 200 according to the invention as per one exemplary embodiment. Here, this can be a manual dispenser similar to the one from FIGS. 7a and 7b. The main body 201 has a cable holding space 185, the volume of which can be the same as the one in the manual dispenser from FIGS. 7a and 7b. A printed circuit board cable device 210 is arranged in the cable holding space 185 of the manual dispenser 200, with the cable holding space 185 consisting of three subspaces 186, 187 and 188. By way of example, this printed circuit board cable device 210 can correspond to the printed circuit board cable device 100 from FIG. 6a by virtue of the annular section 114 of the printed circuit board cable device 100 of the third printed circuit board section 213 being arranged in the third holding space 186, the two branch sections 110, 111 being arranged in the second holding space 187 as second printed circuit board section 212 and the section 103 of the printed circuit board cable device 100 being arranged in the first holding space 188 as first printed circuit board section 211.

The printed circuit board cable device 210 has a printed circuit board (211, 212, 213) with a first printed circuit board section 211, a second printed circuit board section 212 and a third printed circuit board section 213. The third printed circuit board section 213 is arranged at right angles to the first printed circuit board section 211. As a result of a two-ply, stacked arrangement of the conductor tracks of the printed circuit board in region B of the second printed circuit board section 212 and in the narrow implementability of this region, a significantly larger number of contact fields are addressed in the laboratory sample instrument 200 according to the invention than was possible and is the case in known instruments. As a result of this, use can be made in the laboratory sample instrument 200 of syringes and other means 181' in which samples can be held, or adapters, which can be connected to these means, in which the encoding profile has a relatively large number, e.g. NA=14, of profile elevation points, by means of which a logical zero or one can be represented such that an encoding word of 14 bit emerges. As a result of the teaching according to the invention, it is readily possible to increase this number and implement this by technical means without there being space problems in regions of the end face of the manual dispenser 200.

FIG. 10a shows a part of a mounting device for mounting a dispenser syringe 481 of a preferred embodiment of the laboratory sample instrument 400, a handheld dispenser. The mounting device is arranged in a first position, where the dispenser syringe is not mounted at the movable contact socket 411. The contact socket 411, and the third printed circuit board section (not shown), which is firmly connected to the contact socket 411, are parts of the electric sensor apparatus, which identifies the type of syringe, which is connected to the laboratory sample instrument. The mounting device is a snap-in mechanism with two clamp members 412a and 412b, which are arranged on opposing sides of the length axis Z of the laboratory sample instrument in the second and third instrument section and spring mounted by spring 413. The contact socket 411 is movable only along the Z-axis, and guided by a guiding mechanism, and is, furthermore, spring mounted to the dispenser 400, here by four springs 414. The movement of the contact socket 411 is limited by the holding device 415, which is configured to be a block device, which blocks the movement of the contact socket 411.

The holding device has two holding members 415 mounted in opposite to each other, arranged on opposing sides of the length axis Z of the laboratory sample instrument. In the drawings, only one of the two holding members 415 is visible. The one of the holding members 415, which is shown, is arranged between the two branch sections of the second printed circuit board sections 432a and 432b of the printed circuit board cable device 430. Although there is limited space available in the second instrument section, the second printed circuit board sections 432a and 432b can be arranged in the second instrument section. This is because in the second printed circuit board section, at least one conductor track is arranged on the first side of the board and at least one conductor track is arranged on the second side of the board. This way, the width dimension of the second printed circuit board section can be held small, and the problems of space limitation are overcome.

FIG. 10b shows the mounting device of FIG. 10a, where the dispenser syringe is mounted. Here the contact socket 411 is shifted upwards, in the drawings, indicated by the arrows between the lines L1 and L2. The springs 414 are compressed by the syringe 481, which is arrested in the mounting position, in FIG. 10b. The recess between the branch sections 432a and 432b allows the relative movement of the second and third printed circuit board section relative to the holding member 415, which is firmly mounted at the dispenser 400. It should be noted, that the first printed circuit board section 431 is firmly mounted to the dispenser by the mounting hole 433, which means that the second printed circuit board section, shown substantially between lines L1 and L2, will slightly bend by the displacement, when the contact socket 411 is shifted upwardly from the position in FIG. 10a to the second position in FIG. 10b.

Using such an arrangement of FIGS. 10a and 10b, the sensor apparatus arranged at the end face of the dispenser, which end face is formed by the contact socket 411, can be connected to a control device (not shown in FIGS. 10a, 10b) of the dispenser even under limited space conditions inside the dispenser. In other words, the dispenser can be constructed compact and functional at the same time.

The invention claimed is:

1. Laboratory sample instrument (200), more particularly a dispenser or a pipette, comprising:
  a cable holding space (185) in which a printed circuit board cable device (1; 10; 20; 30; 40; 50; 60; 70; 80; 80'; 90; 100; 210; 300) is arranged,
  with the printed circuit board cable device having at least one printed circuit board (2; 12; 22; 32; 42; 52; 62; 72; 82; 92; 102; 211, 212, 213), which has a first and a second side of the board, and, arranged in succession, at least one first printed circuit board section (A; 211), at least one second printed circuit board section (B; 212) and at least one third printed circuit board section (C; 213), with the printed circuit board having a number of conductor tracks (3, 4, 5, 6; 33, 35, 36; 46; 56; 66, 67; 76b, 77b, 76a, 77a; 86, 86b, 87, 87b; 87; 96; 121, 122, 121a, 122a, 121b, 122b) which, at least in sections, are arranged parallel with respect to one another on the printed circuit board and extend from a first track section, which is arranged in the first printed circuit board section, via the second printed circuit board section to the third printed circuit board section, in which a second track section is arranged, wherein the printed circuit board is configured such that in the second printed circuit board section, at least one conductor track (66; 76a, 76b; 86, 87b; 121a, 122a) is arranged on the first side of the board and at least one conductor track (67; 77a, 77b; 86b, 87; 121b, 122b) is arranged on the second side of the board, resulting in a stack of conductor tracks or a multiple-ply second printed circuit board section,
  wherein the third printed circuit board section has a substantially annular or annular-segment-like design or an annular or annular-segment-like segment.

2. Laboratory sample instrument according to claim 1, characterized in that the cable holding space being subdivided into at least one first (188), second (187) and third (186) holding space, with the first (211) printed circuit board section being arranged in the first holding space (188), the second (212) being arranged in the second holding space (187) and the third (213) being arranged in the third holding space (186), the second holding space, when considered perpendicular to the printed circuit board (211, 212, 213), having a smaller cross-sectional area than the first holding space.

3. Laboratory sample instrument according to claim 1, characterized in that it has a first, second and third instrument section, in which respectively the first, second and third holding space are arranged, the printed circuit board cable device bringing about an electric connection between an electric apparatus arranged in the first instrument section and a sensor apparatus arranged in the third instrument section, with contacts preferably being provided at the ends of the conductor tracks in the third printed circuit board section, which contacts are associated with the sensor apparatus by virtue of the closing of an electric circuit being detectable by a conductive contact element contacting the contact.

4. Laboratory sample instrument according to claim 1, characterized in that the at least one first printed circuit board section has a first width dimension (B1; b1) and the at least one second printed circuit board section has a second width dimension (B2; b2), the second width dimension being less than the first width dimension.

5. Laboratory sample instrument according to claim 1, characterized in that, in the second printed circuit board section, the conductor tracks are distributed over the first and second side of the board in substantially equal numbers.

6. Laboratory sample instrument according to claim 1, characterized in that, in the first printed circuit board section, the majority of conductor tracks or all conductor tracks are arranged on the first side of the board, at least in sections.

7. Laboratory sample instrument according to claim 1, characterized in that the second printed circuit board section has at least two branch sections arranged next to one another, within which respectively a number of conductor tracks are arranged, with the sum of the width dimensions of the branch sections corresponding to the second width dimension.

8. Laboratory sample instrument according to claim 1, characterized in that the second printed circuit board section has two branch sections arranged next to one another and the third printed circuit board section is substantially embodied as an annular ring, with the first and second branch section respectively leading to a different half of the annular ring.

9. Laboratory sample instrument according to claim 1, characterized in that the conductor tracks that run on the first side of the board in the third printed circuit board section respectively lead to a contact and those conductor tracks that run on the second side of the board in the third printed circuit board section are routed to the first side of the board through through-holes (131) in the printed circuit board and there respectively lead to a contact face, with the contacts being arranged at a distance from one another on the first side of the board.

10. Laboratory sample instrument according to claim 9, characterized in that the contact consists of first, electrically interconnected contact conductor tracks and second, electrically interconnected contact conductor tracks, the first contact conductor tracks being electrically connected to a conductor track on the printed circuit board and the second contact conductor tracks being electrically connected to another conductor track on the printed circuit board and the first and second contact conductor tracks not being electrically connected, being arranged in meandering intercalated fashion and being electrically interconnectable by an electrically conductive contact element contacting the contact.

\* \* \* \* \*